(12) United States Patent
Vautravers et al.

(10) Patent No.: US 8,987,497 B2
(45) Date of Patent: Mar. 24, 2015

(54) PROCESS FOR THE OXIDATION OF ORGANIC CARBONYL COMPOUNDS

(71) Applicant: BASF SE, Ludwigshafen (DE)

(72) Inventors: Nicolas Vautravers, Mannheim (DE); Joaquim Henrique Teles, Waldsee (DE); Andrei-Nicolae Parvulescu, Heidelberg (DE); Ulrich Müller, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/072,179

(22) Filed: Nov. 5, 2013

(65) Prior Publication Data

US 2014/0128622 A1    May 8, 2014

Related U.S. Application Data

(60) Provisional application No. 61/722,272, filed on Nov. 5, 2012.

(51) Int. Cl.
| | |
|---|---|
| *C07C 69/74* | (2006.01) |
| *C07D 313/04* | (2006.01) |
| *C07C 51/285* | (2006.01) |
| *C07D 309/30* | (2006.01) |
| *C07D 313/00* | (2006.01) |
| *B01J 23/00* | (2006.01) |
| *C07C 45/54* | (2006.01) |

(52) U.S. Cl.
CPC ............ *C07D 313/04* (2013.01); *C07C 51/285* (2013.01); *C07D 309/30* (2013.01); *C07D 313/00* (2013.01); *B01J 23/00* (2013.01); *C07C 45/54* (2013.01)
USPC .......................................... 560/1

(58) Field of Classification Search
USPC ............................................. 560/1
See application file for complete search history.

(56) References Cited

U.S. PATENT DOCUMENTS

| | | |
|---|---|---|
| 5,968,473 A | 10/1999 | Valencia et al. |
| 6,306,364 B1 | 10/2001 | Valencia et al. |
| 7,326,401 B2 | 2/2008 | Tatsumi et al. |

FOREIGN PATENT DOCUMENTS

| | | |
|---|---|---|
| WO | WO-01/81291 A2 | 11/2001 |
| WO | WO-03/074422 A1 | 9/2003 |

OTHER PUBLICATIONS

Liu, G., et al., "Hydrothermal Synthesis of MWW-Type Stannosilicate and its Post-Structural Transformation to MCM-56 Analogue", Microporous and Mesoporous Materials, 2013, vol. 165, pp. 210-218.
Corma, A., et al., "Sn-Zeolite Beta as a Heterogeneous Chemoselective Catalyst for Baeyer-Villiger Oxidations", Nature, 2001, vol. 412, pp. 423-425.
Corma, A., et al,, "A New, Alternative, Halogen-Free Synthesis for the Fragrance Compound Melonal Using Zeolites and Mesoporous Materials as Oxidation Catalysts", Journal of Catalysts, 2005, vol. 234, pp. 96-100.
Kosswig, K., et al., "Oxydation von Cyclododecanon Nach Baeyer Und Villiger", Justus Liebigs Ann. Chem., 1965, vol. 681, pp. 28-30.
International Search Report and Written Opinion for PCT/EP2013/073018 dated May 28, 2014.

*Primary Examiner* — Nizal Chandrakumar
(74) *Attorney, Agent, or Firm* — Drinker Biddle & Reath LLP

(57) ABSTRACT

A process for the oxidation of an organic carbonyl compound comprising reacting the organic carbonyl compound, optionally in the presence of a solvent, with hydrogen peroxide in the presence of a catalyst comprising a tin-containing zeolitic material having an MWW-type framework structure.

20 Claims, No Drawings

PROCESS FOR THE OXIDATION OF ORGANIC CARBONYL COMPOUNDS

CROSS-REFERENCE TO RELATED APPLICATIONS

This application claims benefit (under 35 USC 119(e)) of U.S. Provisional Application No. 61/722,272, filed Nov. 5, 2012, which is incorporated by reference.

The present invention relates to a process for the oxidation of an organic carbonyl compound, in particular a Baeyer-Villiger-type oxidation of an organic carbonyl compound, in the presence of a catalyst comprising a tin-containing zeolitic material having an MWW-type framework structure which zeolitic material has a low boron content.

Oxidation reactions of organic compounds and in particular the Bayer-Villiger reaction is of considerable interest in order to convert readily available carbonyl compounds in more complex and valuable products.

The use of peroxyacetic acid in the Baeyer-Villiger oxidation as described in Justus Liebigs Ann. Chem. 681 (1965), pages 28-30 is a common method for the oxidation of ketones to the respective lactones. However, the use of peroxyacetic acid involves considerable disadvantages regarding cost-effectiveness and safety aspects, in particular in industrial-scale processes.

In Nature 412 (2001), pages 423-425, and in Journal of Catalysis 234 (2005), pages 96 to 100, a tin-containing zeolite Beta is described for the use in the Baeyer-Villiger reaction. Further, in Journal of Catalysis 234 (2005), pages 96-100, a Baeyer-Villiger reaction is disclosed wherein citral is used as starting material. The experiments carried out regarding this reaction show that by use of the tin-containing zeolite Beta a selectivity to melonal of at most 20% is achieved. Generally, tin-containing zeolite Beta materials are comparatively difficult to prepare which renders this prior art process disadvantageous since the synthesis of the catalyst, disclosed in U.S. Pat. No. 5,968,473 and U.S. Pat. No. 6,306,364, is technically difficult to scale-up due to low yield, high synthesis times of more than 15 days, the use of HF and chlorinated Sn precursor compounds.

WO 03/074422 A1 and U.S. Pat. No. 7,326,401 B2 describe a process for synthesizing a zeolite material having MWW structure. A tin-containing MWW is mentioned in the description, having a very high tin loading of about 4.7 weight-%. This tin-containing MWW is prepared from a boron-containing (B-MWW) zeolite precursor which is deboronated by acid treatment before the Sn is introduced.

WO 03/074422 A1 and U.S. Pat. No. 7,326,401 B2 describe a process for synthesizing a zeolite material having MWW structure. A tin containing MWW is mentioned in the description, having a very high tin loading of about 4.7 weight-%. This tin containing MWW is prepared from a B-MWW zeolite precursor which is deboronated by acid treatment before the Sn is introduced.

Thus, it was an object of the present invention to provide a process for the oxidation of an organic carbonyl compound, in particular a Baeyer-Villiger-type oxidation, which does not exhibit the disadvantages of the methods according to the prior art and wherein a high conversion of the starting material as well as a high selectivity to the oxidation product is achieved.

Surprisingly, it was found that by a process for the oxidation of an organic carbonyl compound in the presence of a tin-containing zeolitic material having an MWW-type framework structure and a low boron content, preferably also a low tin content, a high conversion of the starting material and at the same time also a high selectivity of the oxidation product relative to the respective starting material was achieved.

Therefore, the present invention relates to a process for the oxidation of an organic carbonyl compound of formula (I)

(I)

wherein $R_1$ and $R_2$ are independently from one another a linear or branched alkyl residue, a linear or branched alkenyl residue, an aryl or heteroaryl residue, or a hydrogen atom, with the proviso that $R_1$ and $R_2$ are not simultaneously a hydrogen atom, said process comprising (i) reacting the compound of formula (I), optionally in the presence of a solvent, with hydrogen peroxide in the presence of a catalyst comprising a tin-containing zeolitic material having an MWW-type framework structure (Sn-MWW), to obtain a compound of formula (II)

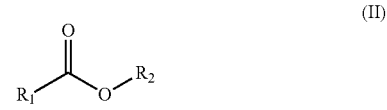

(II)

wherein, if neither $R_1$ nor $R_2$ is a hydrogen atom, $R_1$ and $R_2$ may form together with the carbonyl group or the carboxyl group a ring and the compound of formula (I) is

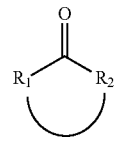

and the compound of formula (II) is

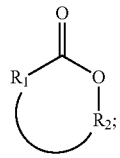

wherein the Sn-MMW framework structure comprises $SiO_2$ and $B_2O_3$ and the molar ratio of $B_2O_3$ relative to $SiO_2$ is at most 0.0025:1.

Preferably, $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom. Preferably, if neither $R_1$ nor $R_2$ is a hydrogen atom, $R_1$ and $R_2$ may form together with the carbonyl group or the carboxyl group a ring having from 4 to 20 carbon atoms.

Generally, there are no specific restrictions as far as the chemical nature of the residues $R_1$ and $R_2$ is concerned provided that the compound of formula (I) can be oxidized to obtain the compound of formula (II). Preferably, as mentioned above, $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom, with the proviso that $R_1$ and $R_2$ are not simultaneously a hydrogen atom.

The linear or branched alkyl residue having from 1 to 20 carbon atoms may be suitably substituted, for example with either at least one halogen atom such F, Cl, Br, I, and/or with at least one alkenyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the linear or branched alkyl residue having from 1 to 20 carbon atoms and which is substituted with at least one alkyl group. The term "heteroaralkyl group" as used in this context of the present invention relates to a heteroaryl group which is bound to the linear or branched alkyl residue having from 1 to 20 carbon atoms, either via a carbon atom or a suitable heteroatom of the heteroaryl group, and which is substituted with at least one alkyl group. Further, the linear or branched alkyl residue having from 1 to 20 carbon atoms may comprise at least one heteroatom, preferably N, O, or S, in the carbon atom chain.

Preferably, the linear or branched alkyl residue has from 1 to 18, more preferably from 1 to 14, more preferably from 1 to 12, more preferably from 1 to 11, more preferably from 1 to 10, more preferably from 1 to 9 carbon atoms, more preferably from 1 to 8 carbon atoms such as 1, 2, 3, 4, 5, 6, 7, or 8 carbon atoms.

The linear or branched alkenyl residue having from 2 to 20 carbon atoms may be suitably substituted, for example with either at least one halogen atom such F, Cl, Br, I, and/or with at least one alkyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the linear or branched alkenyl residue having from 2 to 20 carbon atoms and which is substituted with at least one alkyl group. The term "heteroaralkyl group" as used in this context of the present invention relates to a heteroaryl group which is bound to the linear or branched alkenyl residue having from 2 to 20 carbon atoms, either via a carbon atom or a suitable heteroatom of the heteroaryl group, and which is substituted with at least one alkyl group. Further, the linear or branched alkenyl residue having from 2 to 20 carbon atoms may comprise at least one heteroatom, preferably N, O, or S, in the carbon atom chain.

Preferably, the linear or branched alkenyl residue has from 2 to 18, more preferably from 2 to 14, more preferably from 2 to 12, more preferably from 2 to 11, more preferably from 2 to 10, more preferably from 2 to 9 carbon atoms, more preferably from 2 to 8 carbon atoms such as 2, 3, 4, 5, 6, 7, or 8 carbon atoms.

The aryl or heteroaryl residue having from 4 to 20 carbon atoms may be suitably substituted, for example with either at least one halogen atom such F, Cl, Br, I, and/or with at least one alkyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the aryl or heteroaryl residue having from 4 to 20 carbon atoms and which is substituted with at least one alkyl group. The term "heteroaralkyl group" as used in this context of the present invention relates to a heteroaryl group which is bound to the aryl or heteroaryl residue having from 4 to 20 carbon atoms, either via a carbon atom or a suitable heteroatom of the heteroaryl group, and which is substituted with at least one alkyl group. Further, the heteroaryl residue having from 4 to 20 carbon atoms may comprise, as at least one heteroatom, preferably N, O, or S.

Preferably, the aryl or heteroaryl residue has from 4 to 18, more preferably from 4 to 14, more preferably from 4 to 12, more preferably from 4 to 11, more preferably from 4 to 10, more preferably from 4 to 9 carbon atoms, more preferably from 4 to 8 carbon atoms such as 4, 5, 6, 7, or 8 carbon atoms.

As mentioned above, $R_1$ and $R_2$ are independently from one another a linear or branched alkyl residue, a linear or branched alkenyl residue, an aryl or heteroaryl residue, or a hydrogen atom, with the proviso that $R_1$ and $R_2$ are not simultaneously a hydrogen atom.

Therefore, the compound of formula (I) may comprise a residue $R_1$ which is a linear or branched alkyl residue and a residue $R_2$ which is hydrogen. Further, the compound of formula (I) may comprise a residue $R_1$ which is a linear or branched alkenyl residue and a residue $R_2$ which is hydrogen. Further, the compound of formula (I) may comprise a residue $R_1$ which is an aryl or heteroaryl residue and a residue $R_2$ which is hydrogen. Further, the compound of formula (I) may comprise a residue $R_2$ which is a linear or branched alkyl residue and a residue $R_1$ which is hydrogen. Further, the compound of formula (I) may comprise a residue $R_2$ which is a linear or branched alkenyl residue and a residue $R_1$ which is hydrogen. Further, the compound of formula (I) may comprise a residue $R_2$ which is an aryl or heteroaryl residue and a residue $R_1$ which is hydrogen. Further, the compound of formula (I) may comprise a residue $R_1$ which is a linear or branched alkyl residue and a residue $R_2$ which is a linear or branched alkyl residue. Further, the compound of formula (I) may comprise a residue $R_1$ which is a linear or branched alkenyl residue and a residue $R_2$ which is a linear or branched alkenyl residue. Further, the compound of formula (I) may comprise a residue $R_1$ which is an aryl or heteroaryl residue and a residue $R_2$ which is an aryl or heteroaryl residue. Further, the compound of formula (I) may comprise a residue $R_1$ which is a linear or branched alkyl residue and a residue $R_2$ which is a linear or branched alkenyl residue. Further, the compound of formula (I) may comprise a residue $R_1$ which is a linear or branched alkyl residue and a residue $R_2$ which is an aryl or heteroaryl residue. Further, the compound of formula (I) may comprise a residue $R_1$ which is a linear or branched alkenyl residue and a residue $R_2$ which is an aryl or heteroaryl residue. Further, the compound of formula (I) may comprise a residue $R_2$ which is a linear or branched alkyl residue and a residue $R_1$ which is a linear or branched alkenyl residue. Further, the compound of formula (I) may comprise a residue $R_2$ which is a linear or branched alkyl residue and a residue $R_1$ which is an aryl or heteroaryl residue. Further, the compound of formula (I) may comprise a residue $R_2$ which is a linear or branched alkenyl residue and a residue $R_1$ which is an aryl or heteroaryl residue. Further, it is conceivable that the compound of formula (I) may be a mixture of two or more of these compounds.

Further, if neither $R_1$ nor $R_2$ is a hydrogen atom, $R_1$ and $R_2$ may form, together with the carbonyl group or the carboxyl group according to formula (I), a ring, preferably having from 4 to 20 carbon atoms. The term "a ring having from 4 to 20 carbon atoms" as used in the context of the present invention relates to a ring with a carbon atom chain length of from 4 to 20 carbon atoms.

Preferably, the ring has from 4 to 18, more preferably from 4 to 16, more preferably from 4 to 14, more preferably from 4 to 12 carbon atoms such as 4, 5, 6, 7, 8, 9, 10, 11, or 12 carbon atoms.

The ring may be suitably substituted, for example with either at least one halogen atom such F, Cl, Br, I, and/or with at least one alkyl group preferably having from 2 to 8 carbon atoms, and/or with at least one aryl group or heteroaryl group preferably having from 4 to 10 carbon atoms wherein the at least one heteroatom comprised in the heteroaryl group is preferably S, O, or N, and/or with at least one aralkyl group having from 4 to 10 carbon atoms, and/or with at least one heteroaralkyl group having from 4 to 10 carbon atoms wherein the at least one heteroatom comprised in the heteroaralkyl group is preferably S, O, or N. The term "aralkyl group" as used in this context of the present invention relates to an aryl group which is bound to the ring and which is substituted with at least one alkyl group. The term "heteroaralkyl group" as used in this context of the present invention relates to a heteroaryl group which is bound to the ring, either via a carbon atom or a suitable heteroatom of the heteroaryl group, and which is substituted with at least one alkyl group. Further, the ring may comprise at least one heteroatom, preferably N, O, or S, in the carbon atom chain. Further, the chain of carbon atoms forming the ring together with the carbonyl or carboxyl group according to formula (I) may comprise at least one C—C double bond. Further, it is conceivable that the compound of formula (I) may be a mixture at least compound having a ring formed together with the carbonyl group or the carboxyl group according to formula (I) and at least one compound not having such ring.

According to an embodiment of the present invention, the compound of formula (I) contains at least one C—C double bond. This at least one C—C double bond may be located anywhere in the residues $R_1$ and/or $R_2$ or in the ring formed together with the carbonyl group or the carboxyl group according to formula (I). For example, depending on the size of $R_1$ and/or $R_2$ or in the ring formed together with the carbonyl group or the carboxyl group according to formula (I), the compound of formula (I) may comprise 1, 2, 3 or more C—C double bonds.

Surprisingly, it was found that even if the compound of formula (I) contains a C—C double bond in alpha position to the carbonyl group according to formula (I), i.e. the compound of formula (I) is an alpha, beta unsaturated compound, are subjected to the reaction according to step (i) of the present, a high product selectivity and as well as a high conversion of the starting material is achieved. Therefore, the present invention relates to the process as described above, wherein the compound of formula (I) contains a C—C double bond on alpha position to the carbonyl group. In addition to the C—C double bond in alpha position to the carbonyl group according to formula (I), the compound of formula (I) may comprise 1, 2 or more additional C—C double bonds.

The Sn-MWW Catalyst

As mentioned above, the catalyst used in (i) comprises a tin-containing zeolitic material having an MWW-type framework structure (Sn-MWW). Concerning the catalyst comprising the tin-containing zeolitic material having an MWW-type framework structure, generally, there are no specific restrictions how the tin-containing zeolitic material is provided, with the proviso that the framework structure is an MWW-type framework structure, the framework structure comprises $SiO_2$ and $B_2O_3$ and the molar ratio of $B_2O_3$ relative to $SiO_2$ ($B_2O_3:SiO_2$) is at most 0.0025:1.

Preferably, at least 95 weight-%, more preferably at least 98 weight-%, more preferably at least 99 weight-%, more preferably at least 99.5 weight-%, more preferably at least 99.9 weight-% of the framework structure of the Sn-MWW consist of $B_2O_3$ and $SiO_2$ and optionally Sn. In particular, the Sn-MWW used in (i) is free of aluminum which, in the context of the present invention, relates to a Sn-MWW which may contain aluminum only in traces as impurity.

Preferably, the molar ratio of $B_2O_3$ relative to $SiO_2$ ($B_2O_3:SiO_2$) is in the range of from 0.0005:1 to 0.0025:1, more preferably from 0.0005:1 to 0.0020:1, more preferably from 0.0005 to 0.0015.

Concerning the tin content of the Sn-MWW, no specific restrictions exist. Preferably, the Sn-MWW has a tin content in the range of from 0.1 to 4.0 weight-%, preferably from 0.1 to 3.0 weight-%, more preferably from 0.1 to 2.5 weight-%. Preferred ranges are, for example, from 0.1 to 1.0 weight-%, from 0.1 to 0.9 weight-%, from 0.1 to 0.8 weight-%, from 0.1 to 0.7 weight-%, from 0.1 to 0.6 weight-%, or from 0.1 to 0.5 weight-%, calculated as element and based on the weight of the Sn-MWW.

Therefore, preferred Sn-MWW according to the present invention have a framework structure of which at least 99 weight-%, more preferably at least 99.5 weight-%, more preferably at least 99.9 weight-% consist of $B_2O_3$ and $SiO_2$ and optionally Sn, a molar ratio of $B_2O_3$ relative to $SiO_2$ in the range of from 0.0005:1 to 0.0025:1, preferably from 0.0005:1 to 0.0020:1, and a tin content in the range of from 0.1 to 2.5 weight-%, calculated as element and based on the weight of the Sn-MWW.

Further preferred Sn-MWW according to the present invention have a framework structure of which at least 99 weight-%, more preferably at least 99.5 weight-%, more preferably at least 99.9 weight-% consist of $B_2O_3$ and $SiO_2$ and optionally Sn, a molar ratio of $B_2O_3$ relative to $SiO_2$ in the range of from 0.0005:1 to 0.0025:1, preferably from 0.0005:1 to 0.0020:1, and a tin content in the range of from 0.1 to 1.0 weight-%, calculated as element and based on the weight of the Sn-MWW.

Further preferred Sn-MWW according to the present invention have a framework structure of which at least 99 weight-%, more preferably at least 99.5 weight-%, more preferably at least 99.9 weight-% consist of $B_2O_3$ and $SiO_2$ and optionally Sn, a molar ratio of $B_2O_3$ relative to $SiO_2$ in the range of from 0.0005:1 to 0.0025:1, preferably from 0.0005:1 to 0.0020:1, and a tin content in the range of from 0.1 to 0.5 weight-%, calculated as element and based on the weight of the Sn-MWW.

Preferably, the tin-containing zeolitic material having an MWW-type framework structure used in (i) is prepared according to a process as described in detail hereinunder.

Preferred Process for Producing the Sn-MWW

Preferably, the Sn-MWW is provided by a process comprising (a) providing a boron-containing zeolitic material having an MWW framework structure comprising $SiO_2$ and $B_2O_3$ (B-MWW);

(b) deboronating the B-MWW by treating the B-MWW provided in (a) with a liquid solvent system having a pH in the range of from 5.5 to 8;

(c) incorporating Sn into the deboronated B-MWW obtained from (b) by a process comprising (c.1) preparing an aqueous synthesis mixture containing the deboronated B-MWW obtained from (b), an MWW template compound, preferably selected from the group consisting of piperidine, hexamethylene imine, N,N,N,N',N',N'-hexamethyl-1,5-pentanediammonium ion, 1,4-bis(N-methylpyrrolidinium)-butane, octyltrimethylammonium hydroxide, heptyltrimethylammonium hydroxide, hexyltrimethylammonium hydroxide, and a mixture of two or more thereof, and a tin source, wherein in the synthesis mixture, the molar ratio of Sn, calculated as $SnO_2$, relative to Si, calculated as $SiO_2$ and contained in the deboronated B-MWW, is in the range of from 0.001:1 to 0.05:1;

(c.2) hydrothermally synthesizing a tin-containing zeolitic material having an MWW-type framework structure from the synthesis mixture obtained from (c.1) thereby obtaining a tin-containing zeolitic material having an MWW-type framework structure in its mother liquor;

(c.3) separating the tin-containing zeolitic material having an MWW-type framework structure obtained from (c.2) from its mother liquor;

(d) treating the tin-containing zeolitic material having an MWW-type framework structure obtained from (c) with an aqueous solution having a pH of at most 5 thereby obtaining the Sn-MWW and separating the Sn-MWW from the aqueous solution.

Step (a)

Generally, there are no specific restrictions how the B-MWW is provided in (a). For example, it may be conceivable to purchase a suitable, commercially available boron-containing zeolitic material having an MWW framework structure. Further, for example, any conceivable process for synthesizing such a zeolite can be employed for providing the zeolitic material. Preferably, the zeolitic material is provided in (a) by a process including hydrothermally synthesizing the zeolitic material starting from suitable sources of $B_2O_3$ and $SiO_2$ in the presence of a suitable template compound, also referred to as structure directing agent.

Preferably, the B-MWW is provided in (a) by a process comprising (a.1) hydrothermally synthesizing a B-MWW precursor from an aqueous synthesis mixture containing a silicon source, preferably ammonia stabilized colloidal silica, a boron source, preferably boric acid, and an MWW template compound, preferably selected from the group consisting of piperidine, hexamethylene imine, N,N,N,N',N', N'-hexamethyl-1,5-pentanediammonium ion, 1,4-bis(N-methylpyrrolidinium)-butane, octyltrimethylammonium hydroxide, heptyltrimethylammonium hydroxide, hexyl-trimethylammonium hydroxide, and a mixture of two or more thereof, to obtain the B-MWW precursor in its mother liquor;

(a.2) separating the B-MWW precursor from its mother liquor, preferably comprising drying the B-MWW, wherein the drying is preferably carried out at a temperature in the range of from 100 to 180° C., more preferably from 110 to 140° C., wherein in the synthesis mixture in (a.1), the molar ratio of B, calculated as $B_2O_3$ and contained in the boron source, relative to Si, calculated as $SiO_2$ and contained in the Si source, is preferably in the range of from 0.4:1 to 0.6:1, more preferably from 0.45:1 to 0.55:1, more preferably from 0.47:1 to 0.52:1;

the molar ratio of the MWW template compound, relative to Si, calculated as $SiO_2$ and contained in the Si source, is preferably in the range of from 0.8:1 to 1.7:1, more preferably from 1.0:1 to 1.5:1, more preferably from 1.1:1 to 1.3:1; and the molar ratio of $H_2O$ relative to Si, calculated as $SiO_2$ and contained in the Si source, is preferably in the range of from 12:1 to 20:1, more preferably from 13:1 to 18:1, more preferably from 14:1 to 16:1.

As far as the silicon source used in (a.1) is concerned, no specific restrictions exist. Preferably, the silicon source is a fumed silica or a colloidal silica such as ammonia-stabilized colloidal silica, with ammonia-stabilized colloidal silica being especially preferred.

As far as the boron source used in (a.1) is concerned, no specific restrictions exist. Preferably, the boron source is boric acid, a borate, in particular a water-soluble borate, a boron halide, boron oxide ($B_2O_3$), with boric acid being especially preferred.

As far as the amounts of silicon source and boron source in (a) are concerned, no specific restrictions exist provided that the B-MWW precursor is obtained. Preferably, the molar ratio of B, calculated as $B_2O_3$ and contained in the boron source, relative to Si, calculated as $SiO_2$ and contained in the Si source, is at least 0.4:1, more preferably in the range of from 0.4:1 to 1:1, more preferably from 0.4:1 to 0.8:1, more preferably from 0.4:1 to 0.6:1, more preferably from 0.45:1 to 0.55:1, more preferably from 0.47:1 to 0.52:1.

As far as the MWW template compound in (a.1) is concerned, no specific restrictions exist provided that the B-MWW precursor is obtained. Preferably, the MWW template compound is selected from the group consisting of piperidine, hexamethylene imine, N,N,N,N',N',N'-hexamethyl-1,5-pentanediammonium ion, 1,4-bis(N-methylpyrrolidinium)-butane, octyltrimethylammonium hydroxide, heptyltrimethylammonium hydroxide, hexyltrimethylammonium hydroxide, and a mixture of two or more thereof. More preferably, the MWW template compound is piperidine.

As far as the amounts of silicon source and MWW template compound in (a.1) are concerned, no specific restrictions exist provided that the B-MWW precursor is obtained. Preferably, in (a), the molar ratio of the MWW template compound, relative to Si, calculated as $SiO_2$ and contained in the Si source, is in the range of from 0.8:1 to 1.7:1, more preferably from 1.0:1 to 1.5:1, more preferably from 1.1:1 to 1.3:1.

As far as the amounts of silicon source and water in (a.1) are concerned, no specific restrictions exist provided that the B-MWW precursor is obtained. Preferably, in (a), the molar ratio of $H_2O$ relative to Si, calculated as $SiO_2$ and contained in the Si source, is in the range of from 12:1 to 20:1, more preferably from 13:1 to 18:1, more preferably from 14:1 to 16:1.

According to (a), the aqueous synthesis mixture is preferably subjected to a hydrothermal synthesis under autogenous pressure, wherein the B-MWW precursor is crystallized during the hydrothermal synthesis. For crystallization purposes, it is conceivable to use at least one suitable seeding material such as a zeolitic material having MWW framework structure. Preferably, the crystallization time is in the range of from 3 to 8 days, more preferably from 4 to 6 days. During hydrothermal synthesis, the crystallization mixture may be stirred.

The stirring rates can be suitably chosen depending, for example, on the volume of the aqueous synthesis mixture, the amount of the starting materials employed, the desired temperature, and the like. For example, the stirring rate is in the range of from 50 to 300 r.p.m. (rounds per minute), such as from 70 to 250 r.p.m. or from 90 to 120 r.p.m.

The temperature applied during the hydrothermal synthesis is preferably in the range of from 160 to 200° C., more preferably from 160 to 190° C., more preferably from 160 to 180° C.

After hydrothermal synthesis, the obtained B-MWW precursor is preferably suitably separated from its mother liquor according to (a.2). All conceivable methods of separating a B-MWW precursor from its mother liquor are possible. These methods include, for example, filtration, ultrafiltration, diafiltration and centrifugation methods or, for instance, spray drying processes and spray granulation processes. A combination of two or more of these methods can be applied.

Preferably, the B-MWW precursor is separated from its mother liquid by filtration, and the thus obtained material, for example in the form of a filter cake, is preferably subjected to washing with at least one suitable washing agent, preferably to washing with water, at a temperature of up to 50° C., preferably from 15 to 50° C., more preferably from 15 to 35° C., more preferably from 20 to 30° C. Subsequently, the filter cake is preferably suspended in a suitable liquid, preferably water, to allow the preferred spray-drying or to ultrafiltration. The solids content of such suspension can be suitably chosen to meet the requirements of the preferred spray-drying or to ultrafiltration. It is also conceivable to separate the B-MWW precursor directly from its mother liquor by spray-drying or spray-granulation, preferably spray-drying. In this case, it is possible to suitably increase the B-MWW precursor content of the mother liquor prior to separation by concentrating the suspension. Concentrating may be achieved, for example, by suitable evaporation. If the drying is accomplished by spray-drying, the drying gas inlet temperature is preferably in the range of from 200 to 250° C., more preferably from 220 to 250° C., and the drying gas outlet temperature is preferably in the range of from 100 to 175° C., more preferably from 120 to 150° C.

If washing is applied, it is preferred to continue the washing process until the washing water has a conductivity of at most 1,000 microSiemens/cm, more preferably of at most 800 microSiemens/cm, more preferably of at most 500 microSiemens/cm.

After separation of the B-MWW precursor from the suspension, preferably by filtration, and preferably after washing, the washed B-MWW precursor is optionally subjected to pre-drying, for example by subjecting to a suitable gas stream such as air, lean air, or technical nitrogen, for a time preferably in the range of from 4 to 10 h, more preferably from 5 to 8 h. Subsequently, the optionally pre-dried filter cake is preferably dried, either by the preferred spray-drying as described above or by conventional drying. Preferably, drying is carried out in a suitable atmosphere such as technical nitrogen, air, or lean air. The conventional drying can be accomplished, for example, in a suitable drying oven, preferably carried out for a period in the range of from 1 to 10 h, more preferably from 2 to 6 h.

After the preferred drying, the B-MWW is subjected to calcination to obtain the B-MWW zeolitic material. During calcination, the MWW template compound is preferably at least partially, more preferably essentially completely removed from the framework structure. Preferred calcination temperatures are the range of from 400 to 700° C., more preferably from 500 to 675° C., more preferably from 550 to 650° C. Preferred atmospheres under which the calcination is carried out include technical nitrogen, air, or lean air. Preferred calcination times are in the range of from 0.5 to 12 h, more preferably from 1 to 10 h, more preferably from 2 to 6 h.

Generally, the framework structure of the zeolitic material provided in (a) comprises $B_2O_3$ and $SiO_2$. Preferably, the suitable sources of $B_2O_3$ and $SiO_2$ as described above are employed in an amount and subjected to hydrothermal synthesis conditions so that at least 95 weight-%, preferably at least 98 weight-%, more preferably at least 99 weight-%, more preferably at least 99.5 weight-% such as at least 99.6 weight-%, at least 99.7 weight-%, at least 99.8 weight-%, or at least 99.9 weight-% of the framework structure of the B-MWW provided in (i) consist of $B_2O_3$ and $SiO_2$. In particular, the B-MWW provided in (i) is free of aluminum which, in the context of the present invention, relates to a B-MWW which may contain aluminum only in traces as impurity.

Generally, the molar ratio $B_2O_3:SiO_2$ of the framework structure of the B-MWW is not specifically restricted. Preferably, the molar ratio $B_2O_3:SiO_2$ of the B-MWW is at least 0.03:1, more preferably in the range of from 0.03:1 to 0.1:1, more preferably from 0.03:1 to 0.09:1, more preferably from 0.03:1 to 0.08:1, more preferably from 0.03:1 to 0.07:1. Thus, conceivable preferred molar ratios $B_2O_3:SiO_2$ are in the range of from 0.03:1 to 0.06:1 or from 0.03:1 to 0.05:1 or from 0.03:1 to 0.04:1 or from 0.04:1 to 0.07:1 or from 0.04:1 to 0.06:1 or from 0.04:1 to 0.05:1 or from 0.05:1 to 0.07:1 or from 0.05:1 to 0.06:1 or from 0.06:1 to 0.07:1.

Step (b)

According to the present invention, the B-MWW, especially preferably the separated, dried, preferably spray-dried, and calcined B-MWW provided in (a), is preferably subjected to deboronation in (b) by a treatment with a liquid solvent system having a pH in the range of from 5.5 to 8.

Generally, no specific restrictions exist concerning the chemical nature of the liquid solvent system used in (b). Preferably, the liquid solvent system used in (b) is selected from the group consisting of water, monohydric alcohols, polyhydric alcohols, and mixtures of two or more thereof. Concerning the monohydric alcohols and polyhydric alcohols, no specific restrictions exist. Preferably, these alcohols contain from 1 to 6 carbon atoms, more preferably from 1 to 5 carbon atoms, more preferably from 1 to 4 carbon atoms, and more preferably from 1 to 3 carbon atoms. The polyhydric alcohols preferably comprise from 2 to 5 hydroxyl groups, more preferably from 2 to 4 hydroxyl groups, preferably 2 or 3 hydroxyl groups. Especially preferred monohydric alcohols are methanol, ethanol, and propanol like 1-propanol and 2-propanol. Especially preferred polyhydric alcohols are ethane-1,2-diol, propane-1,2-diol, propane-1,3-diol, and propane-1,2,3-triol. If mixtures of two or more of the above-described compounds are employed, it is preferred that these mixtures comprise water and at least one monohydric and/or at least one polyhydric alcohol. Most preferably, the liquid solvent system used in (b) consists of water.

Further, it is especially preferred that the liquid solvent system does not contain an inorganic acid or an organic acid, or a salt thereof, the acid being selected from the group consisting of hydrochloric acid, sulfuric acid, nitric acid, phosphoric acid, formic acid, acetic acid, propionic acid, oxalic acid, and tartaric acid. Therefore, the present invention also relates to the process above, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, and wherein the liquid solvent system does not contain an inorganic or organic acid, or a salt thereof, the acid being selected from the group consisting of hydrochloric acid, sulfuric acid, nitric acid, phosphoric acid, formic acid, acetic acid, propionic acid, oxalic acid, and tartaric acid. Even more preferably, in (ii), the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, wherein the liquid solvent system does not contain an inorganic or organic acid, or a salt thereof.

As far as the amount of B-MWW which is employed in (b) relative to the amount of liquid solvent system is concerned, no specific restrictions exist. Preferably, the weight ratio of the liquid solvent system relative to B-MWW is in the range of from 40:1 to 5:1, more preferably from 30:1 to 7:1, more preferably from 20:1 to 10:1.

The treating conditions according to (b) are not specifically restricted, provided that the solvent system described above is in its liquid state. In particular, concerning the preferred temperatures described below, the skilled person will choose the respective pressure under which the treating is carried out in order to keep the solvent system in its liquid state. Preferably, in (ii), the treating is carried out at a temperature in the range of from 50 to 125° C., more preferably from 90 to 115° C., more preferably from 95 to 105° C.

Concerning the duration of the treatment according to (b), no specific restrictions exist. The above mentioned time is to be understood as the time for which the liquid solvent system is maintained under the above-described treating temperature. Preferably, in (b), the treating is carried out for a period in the range of from 6 to 20 h, more preferably from 7 to 17 h, more preferably from 8 to 12 h.

As to the type of vessel in which the treatment in (b) is conducted, no particular restrictions exist. Preferably, the vessel is suitably selected to allow to treat the zeolitic material at the temperatures described above, at which temperatures the solvent system is in its liquid state. Therefore, as far as higher temperatures are concerned, in (b), the treating is carried out in a closed system under autogenous pressure.

Further, according to an alternative preferred embodiment of the present invention, in (b), the treating is carried out in an open system under reflux. Thus, the preferred vessel, representing an open system, used for the treating according to (b) is preferably equipped with a reflux condenser.

During the treatment in (b), the temperature of the liquid solvent system is kept essentially constant or is changed, the treating with the liquid solvent system thus being carried out at two or more different temperatures. Most preferably, the temperature is kept essentially constant within the above-defined ranges.

During the treatment according to (b), it is further preferred to suitably stir the liquid solvent system. During (ii), the stirring rate is kept essentially constant or changed, the treating with the liquid solvent system according to (b) thus being carried out at two or more different stirring rates. Most preferably, the B-MWW is suspended in the liquid solvent system at a first stirring rate, and during the treating at the above-described temperatures, the stirring rate is changed, preferably increased. The stirring rates can be suitably chosen depending, for example, on the volume of the liquid solvent system, the amount of the B-MWW employed, the desired temperature, and the like. Preferably, the stirring rate under which the treating of the B-MWW at the above-described temperatures is carried out is in the range of from 50 to 300 r.p.m. (rounds per minute), more preferably from 150 to 270 r.p.m., more preferably from 240 to 260 r.p.m.

According to a conceivable embodiment of the present invention, the treating according to (b) may be carried out in two or more steps wherein between at least two steps, the zeolitic material obtained from a given treating according to (b) is subjected to drying, preferably at a temperature in the range of from 90 to 200° C., more preferably from 100 to 150° C., and the thus dried material is subjected to a further treating according to (b). As to the individual treating steps according to (b) and the conditions applied, full reference is made to the conditions as described above. Concerning the treating time, the sum of the treating times of the individual steps are to be understood as the treating time described above. For each of the at least 2 individual treating steps, the same or different treating conditions can be applied. Therefore, the present invention relates to above-defined process and zeolitic material obtainable or obtained therefrom, wherein the treating according to (b) is carried out in at least 2 separate steps, wherein between at least 2 treating steps, the zeolitic material is dried, preferably at a temperature in the range of from 100 to 150° C. Suitable drying atmospheres include technical nitrogen, air, or lean air.

After the treating according to (b), the obtained deboronated B-MWW is suitably separated from the suspension. All methods of separating the deboronated B-MWW from the respective suspension are conceivable. These methods include filtration, ultrafiltration, diafiltration and centrifugation methods or, for instance, spray-drying processes and spray granulation processes. A combination of two or more of these methods can be applied. According to the present invention, the deboronated B-MWW is preferably separated from the suspension by filtration. Preferably, a filter cake is obtained which is preferably subjected to washing, preferably with water. If washing is applied, it is preferred to continue the washing process until the washing water has a conductivity of at most 1,000 microSiemens/cm, more preferably of at most 750 microSiemens/cm, more preferably of at most 500 microSiemens/cm In general, the process of the present invention can optionally comprise further steps for the work-up and/or further physical and/or chemical transformation of the deboronated B-MWW obtained in (b). The obtained zeolitic material can for example be subject to any sequence of isolation and/or washing procedures, wherein the zeolitic material is preferably subjected to at least one isolation and at least one washing procedure.

After separation of the deboronated B-MWW from the suspension, preferably achieved via filtration, and after washing, the washed filter cake containing the deboronated B-MWW is optionally subjected to drying, for example by subjecting the filter cake to a suitable gas stream such as air, lean air, or nitrogen, preferably a nitrogen stream. Thus, according to a particular preferred embodiment of the present invention, (b) comprises drying the deboronated B-MWW, the drying preferably being carried out at a temperature in the range of from 100 to 180° C., more preferably from 110 to 140° C. Concerning the duration of drying no specific restrictions exist. Preferably, drying is carried out for a period in the range of from 1 to 30 h, more preferably from 14 to 18 h. If spray-drying is carried out, it is conceivable to subject the liquid solvent system containing the zeolitic material, optionally after concentration, directly to spray-drying. Further, it is conceivable to subject the separated and washed zeolitic material to spray-drying, optionally after suitable re-suspending of the washed and optionally pre-dried zeolitic material.

Optionally, stage (b) comprises the calcination of the separated and preferably dried deboronated B-MWW, wherein the calcination is preferably carried out at a temperature in the range of from 400 to 800° C., more preferably from 600 to 700° C. Preferred atmospheres under which the calcination is carried out include technical nitrogen, air, or lean air. Preferred calcination times are in the range of from 0.5 to 12 h, more preferably from 1 to 10 h, more preferably from 2 to 6 h.

The treatment according to (b) with the liquid solvent system reduces the molar ratio $B_2O_3:SiO_2$ of the zeolitic material framework. Preferably, a deboronated B-MWW is obtained from (b) having a molar ratio $B_2O_3:SiO_2$ of at most 0.0025:1, preferably in the range of from 0.0005:1 to 0.0025:1, more preferably from 0.0005:1 to 0.0020:1.

According to an especially preferred embodiment of the present invention, the zeolitic material obtained from (b) is in the form of a powder, preferably in the form of a spray powder wherein the spray-powder may result either from spray-drying in (a) and/or spray-drying in (b), as described above. Preferably, spray-drying is carried out in (a), and no spray-drying is carried out in (b).

Step (c)

The preferably separated and dried, and optionally calcined, deboronated B-MWW obtained from (b) is further subjected to step (c) wherein tin is introduced into the material to obtain a tin-containing zeolitic material. In particular, in (c), tin is introduced into the deboronated B-MWW obtained from (b) by a process comprising (c.1) preparing an aqueous synthesis mixture containing the deboronated B-MWW obtained from (b), an MWW template compound, preferably selected from the group consisting of piperidine, hexamethylene imine, N,N,N,N',N',N'-hexamethyl-1,5-pentanediammonium ion, 1,4-bis(N-methylpyrrolidinium)butane, octyltrimethylammonium hydroxide, heptyltrimethylammonium hydroxide, hexyltrimethylammonium hydroxide, and a mixture of two or more thereof, and a tin source, wherein in the synthesis mixture, the molar ratio of Sn, calculated as $SnO_2$, relative to Si, calculated as $SiO_2$ and contained in the deboronated B-MWW, is preferably in the range of from 0.001:1 to 0.05:1;

(c.2) hydrothermally synthesizing a tin-containing zeolitic material having an MWW-type framework structure from the synthesis mixture obtained from (c.1) thereby obtaining a tin-containing zeolitic material having an MWW-type framework structure in its mother liquor;

(c.3) separating the tin-containing zeolitic material having an MWW-type framework structure obtained from (c.2) from its mother liquor.

As far as the MWW template compound in (c.1) is concerned, no specific restrictions exist provided that the tin-containing B-MWW is obtained. Preferably, the MWW template compound is selected from the group consisting of piperidine, hexamethylene imine, N,N,N,N',N',N'-hexamethyl-1,5-pentanediammonium ion, 1,4-bis(N-methylpyrrolidinium)-butane, octyltrimethylammonium hydroxide, heptyltrimethylammonium hydroxide, hexyltrimethylammonium hydroxide, and a mixture of two or more thereof. More preferably, the MWW template compound is piperidine.

As far as the tin source used in (c.1) is concerned, no specific restrictions exist provided that Sn is introduced into the deboronated B-MWW. Preferably, the tin source is selected from the group consisting of Sn(IV) salts, Sn(II) salts and a mixture of two or more thereof, more preferably from the group consisting of $SnCl_4$, Sn(IV)-acetate, Sn(IV)-tert-butoxide, $SnBr_4$, $SnF_4$, Sn(IV)-bisacetylacetonate dichloride; Sn(IV)-bisacetylacetonate dibromide, Sn(II)-acetate, Sn(II)-acetylacetonate, Sn(II)-citrate, $SnCl_2$, $SnF_2$, $SnI_2$, $SnSO_4$, and a mixture of two or more thereof. More preferably, the tin source is Sn(IV)-tert-butoxide or Sn(II)-acetate.

Preferably, the molar ratio of Sn, calculated as $SnO_2$, relative to Si, calculated as $SiO_2$ and contained in the deboronated B-MWW, in the synthesis mixture in (c.1) is in the range of from 0.001:1 to 0.05:1, more preferably from 0.001:1 to 0.040:1, more preferably from 0.001:1 to 0.03:1, more preferably from 0.001:1 to 0.020:1, more preferably from 0.001:1 to 0.015, more preferably from 0.001 to 0.010.

Concerning the molar ratio of the MWW template compound relative to Si contained in the deboronated B-MWW in the synthesis mixture in (c.1), no specific restrictions exist. Preferably, the molar ratio of the MWW template compound relative to Si, calculated as $SiO_2$ and contained in the deboronated B-MWW, is in the range of from 1.0:1 to 2.0:1, more preferably from 1.2:1 to 1.8:1, more preferably from 1.4:1 to 1.6:1.

Concerning the molar ratio of $H_2O$ relative to Si contained in the deboronated B-MWW in the synthesis mixture in (c.1), the molar ratio of $H_2O$ relative to Si, calculated as $SiO_2$ and contained in the deboronated B-MWW, no specific restrictions exist. Preferably, the molar ratio of $H_2O$ relative to Si, calculated as $SiO_2$ and contained in the deboronated B-MWW is in the range of from 10:1 to 20:1, more preferably from 12:1 to 18:1, more preferably from 14:1 to 16:1.

The synthesis mixture obtained in (c.1) is subjected to hydrothermally synthesizing a tin-containing zeolitic material having an MWW-type framework structure. It may be conceivable to use at least one suitable seeding material in step (c.2) to obtain the tin-containing zeolitic material contained in its mother liquor. For example, a conceivable seeding material is a zeolitic material having an MWW framework structure. Preferably, the hydrothermal synthesis according to (c.2) is carried out at a temperature in the range of from 80 to 250° C., more preferably from 120 to 200° C., more preferably from 160 to 180° C. Further, the hydrothermal synthesizing according to (c.2) is preferably carried out for a period in the range of from 20 to 200 h, more preferably from 60 to 160 h, more preferably from 110 to 125 h.

During the hydrothermal synthesis according to (c.2), it is preferred to suitably stir the synthesis mixture wherein the stirring rate is kept essentially constant or changed. The stirring rate can be suitably chosen depending, for example, on the volume of the aqueous synthesis mixture, the amount of the zeolitic material employed, the desired temperature, and the like. Preferably, the stirring rate under which the treating of the zeolitic material at the above-described temperatures is carried out is preferably in the range of from 50 to 300 r.p.m. (rounds per minute), more preferably from 70 to 150 r.p.m., more preferably from 90 to 120 r.p.m.

After hydrothermal synthesis, the obtained tin-containing zeolitic material having an MWW-type framework structure is suitably separated from the mother liquor in step (c.3). All methods of separating the tin-containing zeolitic material having an MWW-type framework structure from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the tin-containing zeolitic material having an MWW-type framework structure is preferably separated from its mother liquid by filtration to obtain a filter cake which is preferably subjected to washing, preferably with water.

Prior to separating the tin-containing zeolitic material having an MWW-type framework structure from its mother liquor, it is possible to increase the tin-containing zeolitic material having an MWW-type framework structure content of the mother liquor by concentrating the suspension. If washing as applied, it is preferred to continue the washing process until the washing water has a conductivity of less than 1,000 microSiemens/cm, more preferably of less than 750 microSiemens/cm, more preferably of less than 500 microSiemens/cm.

After separation of the tin-containing zeolitic material having an MWW-type framework structure from its mother liquor, preferably achieved via filtration, and after washing, the washed filter cake containing the tin-containing zeolitic material having an MWW-type framework structure is optionally subjected to pre-drying, for example by subjecting the filter cake to a suitable gas stream, preferably a nitrogen stream, for a time preferably in the range of from 4 to 10 h, more preferably from 5 to 8 h.

Preferably, stage (c.3) comprises drying the tin-containing zeolitic material having an MWW-type framework structure, wherein the drying is preferably carried out at a temperature in the range of from 100 to 180° C., more preferably from 110 to 140° C. Concerning the duration of drying the tin-containing zeolitic material having an MWW-type framework structure, no specific restrictions exist. Preferably, the drying is carried out for a period in the range of from 1 to 30 h, more preferably from 6 to 24 h, more preferably from 14 to 18 h.

While it is generally possible to subject the separated and preferably dried tin-containing zeolitic material having an MWW-type framework structure to calcination, it is especially preferred according to the present invention not to subject the separated and preferably dried tin-containing zeolitic material having an MWW-type framework structure in (c.3) before (d). In this context, the term "calcination" relates to a heating of the tin-containing zeolitic material having an MWW-type framework structure to a temperature of above 450° C. Thus, according to a particular embodiment of the present invention, the separated and preferably dried tin-containing zeolitic material having an MWW-type framework structure obtained in (c.3) is not subjected to calcination before (d).

Step (d)

According to the present invention, the separated and preferably dried tin-containing zeolitic material having an MWW-type framework structure obtained from (c) is subjected to stage (d) wherein the tin-containing zeolitic material having an MWW-type framework structure is treated with an aqueous solution having a pH of at most 5 thereby obtaining the Sn-MWW, and optionally separating the Sn-MWW from the aqueous solution.

Preferably, in (d), the tin-containing zeolitic material having an MWW-type framework structure obtained from (c) is treated with an aqueous solution which comprises an organic acid, preferably selected from the group consisting of oxalic acid, acetic acid, citric acid, methane sulfonic acid, and a mixture of two or more thereof, and/or an inorganic acid, preferably selected from the group consisting of phosphoric acid, sulphuric acid, hydrochloric acid, nitric acid, and a mixture of two or more thereof, the inorganic acid more preferably being nitric acid. Preferably, in (d), the aqueous solution has a pH in the range of from 0 to 5, more preferably from 0 to 3, more preferably from 0 to 2. The pH values are to be understood as being determined with a pH sensitive glass electrode.

Concerning the temperature of the treating with the aqueous solution according to (d), no specific restrictions exist. Preferably, in (d), the tin-containing zeolitic material having an MWW-type framework structure is treated with the aqueous solution at a temperature in the range of from 50 to 175° C., more preferably from 70 to 125° C., more preferably from 95 to 105° C. Preferably, in (iv), the tin-containing zeolitic material having an MWW-type framework structure is treated with the aqueous solution for a period in the range of from 1 to 40 h, more preferably from 12 to 24 h, more preferably from 18 to 22 h.

As far as the weight ratio of the tin-containing zeolitic material having an MWW-type framework structure relative to the aqueous solution is concerned, no specific restrictions exist. Preferably, in (d), the weight ratio of the aqueous solution relative to the tin-containing zeolitic material having an MWW-type framework structure is in the range of from 10:1 to 50:1, preferably from 20:1 to 40:1, more preferably from 25:1 to 35:1.

Concerning the type of vessel in which heating in (d) is conducted, no particular restrictions exist. Preferably, the vessel is suitably selected to allow to treat the zeolitic material at the temperatures described above, at which temperatures the solvent system is in its liquid state. Therefore, as far as higher temperatures are concerned, in (d), the treating is carried out in a closed system under autogenous pressure.

Further, according to an alternative preferred embodiment of the present invention, in (d), the treating is carried out in an open system under reflux. Thus, the preferred vessel, representing an open system, used for the treating according to (d) is preferably equipped with a reflux condenser.

During the treating according to (d), it is preferred to suitably stir the aqueous solution containing the zeolitic material. During (d), the stirring rate is kept essentially constant or changed. The stirring rate can be suitably chosen depending, for example, on the volume of the aqueous solution, the amount of the zeolitic material employed, the desired temperature, and the like. Preferably, the stirring rate under which the treating of the tin-containing zeolitic material having an MWW-type framework structure at the above-described temperatures is carried out is in the range of from 50 to 300 r.p.m. (rounds per minute), more preferably from 100 to 250 r.p.m., more preferably from 180 to 220 r.p.m.

The treatment according to (d) preferably comprises suitably separating the Sn-MWW from the aqueous solution. All methods of separating Sn-MWW from the aqueous solution are conceivable. These methods include, for example, filtration, ultrafiltration, diafiltration and centrifugation methods or, for instance, spray drying processes and spray granulation processes. A combination of two or more of these methods can be applied. According to the present invention, Sn-MWW is preferably separated from the aqueous solution by filtration to obtain a filter cake which is preferably subjected to washing, preferably with water.

If washing as applied, it is preferred to continue the washing process until the washing water has a pH of 7, wherein the pH is to be understood as being determined using a pH sensitive glass electrode.

Preferably, (d) comprises drying the Sn-MWW, wherein the drying is preferably carried out at a temperature in the range of from 100 to 180° C., more preferably from 110 to 130° C. Concerning the duration of drying the Sn-MWW, no specific restrictions exist. Preferably, the drying is carried out for a period in the range of from 1 to 20 h, more preferably from 4 to 16 h, more preferably from 8 to 12 h.

Preferably, the separated and preferably dried Sn-MWW is further subjected to calcination in (d), wherein the calcination is preferably carried out at a temperature in the range of from 400 to 800° C., more preferably from 450 to 700° C., more preferably from 500 to 600° C. Concerning the duration of calcination, no specific restrictions exist. Preferably, the calcination is carried out for a period in the range of from 1 to 20 h, more preferably from 8 to 12 h.

As mentioned above, from (d), a Sn-MWW is obtained with a tin content, preferably in the range of from 0.1 to 4.0 weight-%, preferably from 0.1 to 3.0 weight-%, more preferably from 0.1 to 2.5 weight-%. Preferred ranges are, for example, from 0.1 to 1.0 weight-%, from 0.1 to 0.9 weight-%, from 0.1 to 0.8 weight-%, from 0.1 to 0.7 weight-%, from 0.1 to 0.6 weight-%, or from 0.1 to 0.5 weight-%, calculated as element and based on the weight of the Sn-MWW.

Preferably, a Sn-MWW is prepared according to the preferred process as described above having a tin content of at most 2.0 weight-%, more preferably in the range of from 0.05 to 2.0 weight-%, more preferably from 0.1 to 1.9 weight-%, more preferably from 0.1 to 1.8 weight-%, more preferably from 0.1 to 1.7 weight-%, more preferably from 0.1 to 1.6 weight-%, more preferably from 0.1 to 1.5 weight-%, more preferably from 0.1 to 1.4 weight-%, more preferably from 0.1 to 1.3 weight-%, more preferably from 0.1 to 1.2 weight-%, more preferably from 0.1 to 1.0 weight-%. Conceivable preferred ranges are from 0.15 to 0.9 weight-% or from 0.2 to 0.8 weight-% or from 0.25 to 0.7 weight-% or from 0.3 to 0.6 weight-% or from 0.35 to 0.5 weight-%.

Surprisingly, it was found that the preferred process according to the invention which comprises the incorporation of Sn into a deboronated B-MWW, wherein the amount of Sn is chosen in such a manner that the Sn-MWW obtained from (iv) has a Sn content of at most 2 weight-%, leads to a novel tin-containing zeolitic material having an MWW-type framework structure. Compared to the conventional tin-containing zeolitic material having an MWW framework structure, the novel material is characterized in that it exhibits an increased interlayer distance between the individual layers of the zeolitic material. A specific feature of the novel tin-containing zeolitic material having an MWW-type framework structure is an additional peak in the XRD diffraction pattern at a 2 theta diffraction angle of $(6.6 \pm 0.1)°$.

Therefore, the present invention generally relates to a tin-containing zeolitic material having an MWW-type framework structure and having an X-ray diffraction pattern comprising a peak at a 2 theta diffraction angle of $(6.6 \pm 0.1)°$, preferably having an X-ray diffraction pattern comprising a peak at a 2 theta diffraction angle of $(6.6 \pm 0.1)°$, a peak at a 2 theta diffraction angle of $(7.1 \pm 0.1)°$, and a peak at a 2 theta diffraction angle of $(7.9 \pm 0.1)°$, more preferably an X-ray diffraction pattern comprising peaks at 2 theta diffraction angles of $(6.6 \pm 0.1)°$, $(7.1 \pm 0.1)°$, $(7.9 \pm 0.1)°$, $(9.6 \pm 0.1)°$, $(12.8 \pm 0.1)°$, $(14.4 \pm 0.1)°$, $(14.7 \pm 0.1)°$, $(15.8 \pm 0.1)°$, $(19.3 \pm 0.1)°$, $(20.1 \pm 0.1)$, $°(21.7 \pm 0.1)°$, $(21.9 \pm 0.1)°$, $(22.6 \pm 0.1)°$, $(22.9 \pm 0.1)°$, $(23.6 \pm 0.1)°$, $(25.1 \pm 0.1)°$, $(26.1 \pm 0.1)°$, $(26.9 \pm 0.1)°$, $(28.6 \pm 0.1)°$, and $(29.1 \pm 0.1)°$. This increased interlayer distance is further reflected in the c parameter, determined via XRD, which, for the novel Sn-MWW, is $(27.1 \pm 0.2)$ Angstrom. Compared to the conventional tin-containing zeolitic materials having MWW framework structure, the c parameter of the novel Sn-MWW is increased.

Preferably, at least 95 weight-%, preferably at least 98 weight-%, more preferably at least 99 weight-%, more preferably at least 99.5 weight-%, more preferably at least 99.9 weight-% of the framework structure of the novel Sn-MWW consist of $SiO_2$ and $B_2O_3$ and optionally Sn. In particular, the Sn-MWW is free of aluminum which, in the context of the present invention, relates to a Sn-MWW which may contain aluminum only in traces as impurity. Preferably, the novel Sn-MWW has a BET surface area, determined according to DIN 66131, in the range of from 300 to 600 $m^2/g$, more preferably from 350 to 500 $m^2/g$. Preferably, the novel Sn-MWW has a Langmuir surface, determined according to DIN 66135, in the range of from 400 to 700 $m^2/g$, more preferably from 500 to 600 $m^2/g$.

As mentioned above, it is preferred that in at least one stage of the preferred process for the preparation of the novel Sn-MWW, a spray-drying step is performed. Therefore, it is preferred that the novel Sn-MWW is present in the form of a spray-powder obtained from such spray-drying. Such a spray-powder can be characterized by the Dv10 value, Dv50 value, and/or the Dv90 value, which values are typically at least 1 micrometer. Typical values for Dv10 may be in the range of from 1 to 10 micrometer, typical values for Dv50 may be in the range of from 5 to 50 micrometer, typical values for Dv90 may be in the range of from 20 to 100 micrometer. In this context, the Dv10, Dv50 and Dv90 values are to be understood as being determined according to a method where 1.0 g of a given spray-powder is suspended in 100 g deionized water and stirred for 1 min and then subjected to the measurement in a particle size measurement apparatus Mastersizer S long bed version 2.15, ser. No. 33544-325; (supplier: Malvern Instruments GmbH, Herrenberg, Germany) with the following parameters: focal width 300RF mm; beam length 10.00 mm; module MS17; shadowing 16.9%; dispersion model 3$$D; analysis model polydisperse; correction none.

Further Steps

Treatment of the Sn-MWW with an Aqueous System

Depending on the specific requirements of the oxidation reaction of the present invention, it is conceivable that the Sn-MWW obtained from (d), preferably the separated, dried and calcined Sn-MWW, is subjected to a treatment with an aqueous system having a pH in the range of from 5.5 to 8.

Preferably, the Sn-MWW is treated with the aqueous system at a temperature in the range of from 80 to 220° C., preferably from 100 to 180° C., more preferably from 130 to 150° C. Further, the treating with the aqueous system is preferably carried out for a period in the range of from 1 to 20 h, more preferably from 4 to 15 h, more preferably from 6 to 10 h. Preferably, at least 95 weight-%, more preferably at least 99 weight-%, more preferably at least 99.9 weight-% of the aqueous system consist of water. More preferably, the aqueous system is water. Preferably, the treating with the aqueous system is carried out in a closed system, under autogenous pressure and with or without stirring. According to another embodiment of the present invention, the treating with the aqueous system is carried out in an open system, preferably under reflux, and with or without stirring.

After treating of the Sn-MWW with the aqueous system, the Sn-MWW is preferably suitably separated from the suspension. All methods of separating the Sn-MWW from the suspension are conceivable. These methods include, for example, filtration, ultrafiltration, diafiltration and centrifugation methods or, for instance, spray drying processes and spray granulation processes. A combination of two or more of these methods can be applied. According to the present invention, the Sn-MWW is preferably separated from the suspension by filtration, and the thus obtained Sn-MWW, for example in the form of a filter cake, is preferably subjected to washing, preferably to washing with water, at a temperature in the range of from up to 50° C., more preferably from 15 to 35° C., more preferably from 20 to 30° C. Subsequently, the filter cake, optionally further processed to obtained a suitable suspension, is optionally subjected to spray-drying or to ultrafiltration.

After treating with the aqueous system, the Sn-MWW is preferably subjected to drying and/or calcination, wherein drying is preferably carried out at a temperature in the range of from 100 to 180° C., preferably from 130 to 150° C., for a period in the range of from 10 to 70 h, preferably from 15 to 25 h, and calcination is preferably carried out at a temperature in the range of from 550 to 700° C., preferably from 600 to 680° C., for a period in the range of from 1 to 10 h, preferably from 2 to 5 h.

Therefore, the present invention also relates to the above defined process for the preparation of a Sn-MWW, further comprising (d.1) treating the Sn-MWW obtained from (iv) with an aqueous system having a pH in the range of 5.5 to 8;
(d.2) drying and/or calcining the Sn-MWW obtained from (iv.1).

Preparation of a Molding

Depending on the mode according to which the oxidation process of the present invention is carried out in (i), the catalyst comprising the Sn-MWW is preferably employed as a powder, a spray-powder, or a molding. For example, if the oxidation process of the present invention is carried out in batch mode, it may be preferred to employ the catalyst comprising the Sn-MWW as powder or spray-powder. For example, if the oxidation process of the present invention is carried out in semi-continuous mode or continuous mode, such as in a fixed-bed catalyst mode, it may be preferred to employ the catalyst comprising the Sn-MWW as spray-powder or as molding.

Therefore, depending on the specific mode of the oxidation process of the present invention, it is conceivable that the powder or the spray-powder obtained from (d), optionally from (d.1) or (d.2) is further processed to prepare a molding comprising the powder or the spray-powder.

Therefore, the present invention also relates to the above-defined process, further comprising (e) preparing a moldable mixture comprising the Sn-MWW obtained from (d), the moldable mixture optionally comprising a binder or a binder precursor;
(f) subjecting the mixture obtained from (e) to shaping to obtain a molding containing the Sn-MWW;
(g) optionally drying and/or calcining the molding obtained in (f).

In general, suitable binders are all compounds which impart adhesion and/or cohesion between the zeolitic material particles to be bonded which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaolin, hectorite, bentonites, halloysites, dickites, nacrites or anaxites. These binders can be used as such or in the form of suitable precursor compounds which, either during spray-drying and/or the subsequent calcination form the desired binder. Examples of such binder precursors are tetraalkoxysilanes, tetraalkoxytitanates, tetraalkoxyzirconates or a mixture of two or different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, are preferred. In this context, both colloidal silica and so-called "wet process" silica and so-called "dry process" silica can be used. This silica may be amorphous silica, the size of the silica particles being, for example, in the range of from 5 to 100 nm and the surface area of the silica particles being in the range of from 50 to 500 $m^2/g$. Colloidal silica, preferably as an alkaline and/or ammoniacal solution, more preferably as an ammoniacal solution, is commercially available, inter alia, for example as Ludoxo®, Sytono®, Nalco® or Snowtexo®. "Wet process" silica is commercially available, inter alia, for example as Hi-Silo®, Ultrasilo®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica can be preferred.

As to the ratio of the amount of Sn-MWW relative to the amount of binder used for preparing a molding, it generally can be freely chosen. Generally, the weight ratio of the Sn-MWW relative to binder is in the range of from 20:1 to 1:20, preferably from 10:1 to 1:10, more preferably from 1:1 to 1:10.

For preparing a molding based on the Sn-MWW, at last one pasting agent can be used to provide for an improved processability of the moldable mixture. Conceivable pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, carbohydrates such as cellulose, cellulose derivatives, water and mixtures of two or more of these compounds, such as water and cellulose or water and cellulose derivatives are used as pasting agent. Preferably, the at least one pasting agent is removed by drying and/or calcination, as further described below.

As to the ratio of the amount of Sn-MWW relative to the amount of pasting agent used for preparing a molding, it generally can be freely chosen. Generally, the weight ratio of the Sn-MWW relative to pasting agent is in the range of from 20:1 to 1:50, preferably from 10:1 to 1:40, more preferably from 1:1 to 1:30.

It is further conceivable that a pore-forming agent, in particular a mesopore-forming agent is additionally employed for the preparation of the moldings. Such pore forming agents usually employed are preferably polymeric vinyl compounds, such as, for example, polyalkylene oxides, such as polyethylene oxides, polystyrenes, polyacrylates, polymethacrylates, polyolefins, polyamides and polyesters.

The moldings of the present invention may be shaped in (f) in every conceivable geometry such as strands, for example having rectangular, triangular hexagonal, quadratic, oval, or circular cross-section, stars, tablets, spheres, hollow cylinders, and the like. Depending on the specific geometry, the shaping process according to (f) will be chosen. If, according to a preferred embodiment of the present invention, strands are prepared, the shaping according to (f) preferably comprises subjecting the mixture obtained in (e) to extrusion. Suitable extrusion apparatuses are described, for example, in "Ullmann's Enzyklopädie der Technischen Chemie", 4th edition, vol. 2, page 295 et seq., 1972. In addition to the use of an extruder, an extrusion press can also be used for the preparation of the moldings. If necessary, the extruder can be suitably cooled during the extrusion process. Extrusion processes are conceivable wherein per batch, the power consumption is in the range of from 1 to 10 A, preferably from 1.5 to 6 A, more preferably from 2 to 4 A.

The strands leaving the extruder via the extruder die head can be mechanically cut by a suitable wire or via a discontinuous gas stream.

The molding obtained from (f) is optionally dried and/or calcined. No specific restrictions exist concerning the drying and calcination conditions. The drying is preferably carried out at temperatures in the range of in general from 80 to 160° C., more preferably from 90 to 155° C., more preferably from 100 to 150° C., and preferably for a duration in the range of from 6 to 24 h, more preferably from 8 to 20 h such as from 10 to 20 h. The drying can be effected under any suitable gas atmosphere, wherein nitrogen, air and/or lean air are preferred.

The calcination is preferably carried out at temperatures in the range of in general from 400 to 650° C., more preferably from 450 to 625° C., more preferably from 500 to 600° C., and preferably for a duration in the range of from 0.25 to 6 h, more preferably from 0.5 to 5 h such as from 0.5 to 2 h. The calcination can be effected under any suitable gas atmosphere, wherein air and/or lean air are preferred.

Therefore, the present invention also relates to a molding, preferably an extrudate, comprising the Sn-MWW according to the present invention and optionally at least one binder.

Treatment of the Moldings with an Aqueous System

Further, it is conceivable that the moldings comprising the Sn-MWW obtained from (f) or (g), preferably (g), are subjected to a treatment with an aqueous system having a pH in the range of 5.5 to 8.

Preferably, the moldings are treated with the aqueous system at a temperature in the range of from 80 to 220° C., preferably from 100 to 180° C., more preferably from 130 to 150° C. Further, the treating with the aqueous system is carried out for a period in the range of from 1 to 20 h, preferably from 4 to 15 h, more preferably from 6 to 10 h. Preferably, at least 95 weight-%, more preferably at least 99 weight-%, more preferably at least 99.9 weight-% of the aqueous system consists of water. More preferably, the aqueous system is water.

According to a preferred embodiment of the present invention, the treating with the aqueous system is carried out in a closed system, under autogenous pressure and with or without stirring. According to another embodiment of the present invention, the treating with the aqueous system is carried out in an open system, preferably under reflux, and with or without stirring.

After treating of the moldings with the aqueous system, the moldings are preferably suitably separated from the suspension. All methods of separating the moldings from the suspension are conceivable. These methods include, for example, filtration and centrifugation methods. A combination of two or more of these methods can be applied. According to the present invention, the moldings are preferably separated from the aqueous system by filtration, and the thus obtained moldings are preferably subjected to washing, preferably to washing with water, at a temperature in the range of from up to 50° C., preferably from 15 to 35° C., more preferably from 20 to 30° C.

After treating with the aqueous system, the moldings are preferably subjected to drying and/or calcination, wherein drying is preferably carried out at a temperature in the range of from 100 to 180° C., more preferably from 130 to 150° C., preferably for a period in the range of from 10 to 70 h, more preferably from 15 to 25 h, and calcination is preferably carried out at a temperature in the range of from 550 to 700° C., more preferably from 600 to 680° C., preferably for a period in the range of from 1 to 10 h, more preferably from 2 to 5 h. Therefore, the present invention also relates to the above defined process, further comprising (h) treating the moldings obtained from (f) or (g), preferably (g), with an aqueous system having a pH in the range of 5.5 to 8;

(k) optionally drying and/or calcining the moldings obtained from (h).

The Reaction in (i)

As far as the amount of catalyst is concerned which is employed in (i), no specific restrictions exist. Preferably, the amount of catalyst is chosen so that at the beginning of the reaction, the molar ratio of Sn, calculated as element and contained in the Sn-MWW, relative to the compound of formula (I) is in the range of from 0.001:1 to 0.05:1, preferably from 0.003:1 to 0.3:1, more preferably from 0.005:1 to 0.01:1.

As far as the amount of hydrogen peroxide is concerned which is employed in (i), no specific restrictions exist. Preferably, the amount of hydrogen peroxide is chosen so that at the beginning of the reaction, the molar ratio of Sn, calculated as element and contained in the Sn-MWW, relative to hydrogen peroxide is in the range of from 0.001:1 to 0.05:1, preferably from 0.003:1 to 0.03:1, more preferably from 0.005:1 to 0.015:1.

If the reaction according to (i) is carried out in batch-mode, the term "at the beginning of the reaction" relates to the point in time where all starting materials, including the catalyst, are simultaneously present in the reaction mixture and, depending on the temperature, the conversion of the compound of formula (I) begins. If the reaction according to (i) is carried out in continuous-mode, the term "at the beginning of the reaction" relates to the entrance of the reactor through which the reaction mixtures is passed, where the feed stream or the feed streams fed into the reactor get in contact with the catalyst.

As far as the hydrogen peroxide is concerned, no specific restrictions exist. In particular, the hydrogen peroxide feed can be prepared according to every conceivable method. It is conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back. The preparation of hydrogen peroxide from the elements is also conceivable. Depending on the specific preparation method, the hydrogen peroxide feed can be, for example, an aqueous or an aqueous/methanolic hydrogen peroxide feed. In case an aqueous hydrogen peroxide feed is employed, the content of the aqueous hydrogen peroxide with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. In case an aqueous/methanolic hydrogen peroxide is employed, the content of the aqueous/methanolic hydrogen peroxide with respect to hydrogen peroxide is usually in the range of from 3 to 85 weight-%, preferably from 4 to 25 weight-%, more preferably from 5 to 15 weight-%, and the mass ratio of hydrogen peroxide relative to water is usually at least 0.4, preferably in the range of from 0.4 to 17, more preferably in the range of from 0.6 to 6. According to a preferred embodiment of the present invention, an aqueous hydrogen peroxide is employed.

Concerning the solvent which is optionally employed in (i), no specific restrictions exist. Usually, the skilled person will choose a suitable solvent or solvent mixture depending on the chemical nature of the compound of formula (I), the compound of formula (II), or other requirements of the reaction according to (i). Suitable solvents include, but are not restricted to, acetonitrile, 1,2-dichloroethane, dichloromethane, chloroform, acetonitrile, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof. According to an embodiment of the present invention, the solvent optionally used in (i) is not chlorobenzene. A preferred solvent is 1,2-dichloroethane or acetonitrile.

The reaction conditions used in (i) are not specifically restricted. In particular, concerning the temperature of the reaction mixture according to (i), no specific restrictions exist, provided that it is suitable to obtain the oxidized organic carbonyl compound of formula (II). In particular, the reaction temperature will depend on the presence or absence of a solvent or the chemical nature of the solvent. Preferably, the reaction according to (i) is carried out at a temperature in the range of from 50 to 150° C., preferably from 70 to 120° C., more preferably from 90 to 110° C.

According to the invention, the oxidation reaction according to (i) is generally conducted such that the organic carbonyl compound, in the presence of hydrogen peroxide and optionally in the presence of a solvent is brought into contact with the Sn-MWW in a suitable reaction zone. There is no specific restriction as to the reaction mode provided that it is suitable to obtain the oxidized organic carbonyl compound of formula (II). Accordingly, the inventive process may principally carried out in batch-mode, or in semi-continuous mode, or in continuous mode.

According to an embodiment of the present invention, the reaction according to (i) is carried out in batch-mode. No specific restrictions exist concerning the reaction time which is employed, provided that it is suitable to obtain the oxidized organic carbonyl compound of formula (II). Preferably, the reaction is carried out for a period in the range of from 1 to 10 h, preferably from 3 to 5 h. Preferably, the reaction according to (i) is carried out under reflux if it is carried out in batch-mode. In this case, the suitable reaction zone used in (i) is preferably a vessel equipped with suitable heating means equipped with a reflux condenser. Thus, the reaction according to (i) is preferably carried out in an open system under reflux. During the reaction according to (i), it is preferred to stir the reaction mixture. The stirring rate can be kept essentially constant or changed during (i). The stirring rates can be suitably chosen depending, for example, on the volume of the reaction mixture, the desired temperature, and the like.

According to an embodiment of the present invention, the reaction according to (i) is carried out in continuous-mode. No specific restrictions exist concerning the set-up of the continuous process. Preferred continuous process set-ups include the use of at least one fixed-bed reactor wherein the fixed catalyst bed contains the moldings comprising the Sn-MWW as described above, through which fixed bed the reaction mixture is passed. According to this embodiment, it is possible to feed the individual starting materials, optionally also the solvent, as individual stream into the reactor. It is also possible to suitably combine the individual starting material streams before they are fed to the reactor. For example, it is conceivable to combine the hydrogen peroxide stream with the solvent stream or a portion of the solvent stream and feed this stream to the reactor, wherein the feed containing the compound of formula (I) is fed as separate stream to the reactor, optionally combined with a portion of the solvent stream. Two or more reactors can be employed wherein at least two reactors can be coupled in parallel and/or at least two reactors can be coupled in series. Between two reactors coupled in series, at least one intermediate stage can be realized where, for example, the compound of formula (I) is suitably separated from the reaction mixture and the remaining portion of the reaction mixture, optionally together with one or more fresh starting materials, is fed to the next reactor. If two or more reactors are employed, the catalysts in the reactors can be the same or different from each other provided that they comprise Sn-MWW.

After the reaction according to (i), the used catalyst comprising the Sn-MWW is separated from the reaction mixture. If the reaction is carried out in continuous-mode using a fixed-bed reactor, the reaction mixture leaves the reactor and the catalyst remains in the reactor. If the reaction is carried out in batch-mode, the separation of the catalyst which is preferably employed as powder or spray-powder comprising the Sn-MWW can be achieved by any conceivable method including, for example, filtration, ultrafiltration, diafiltration and centrifugation and/or decantation methods, wherein filtration methods can involve suction and/or pressure filtration steps.

After separation, the separated catalyst is optionally subjected to one ore more washing steps using one or more suitable washing agents. Conceivable washing agents may include water, ethers such as dioxanes such as 1,4-dioxane, alcohols such as methanol, ethanol, propanol, or mixtures of two or more thereof. Preferred washing agents are dioxanes. Preferred temperatures applied during the washing step are in the range of from 10 to 50° C., preferably from 15 to 40° C., more preferably from 20 to 30° C.

Generally, the present invention also relates to a reaction mixture, obtainable or obtained from step (i) of the process as described above, optionally after separation of the catalyst.

Step (ii)

After the reaction according to (i), the obtained compound of formula (II) is preferably separated from the reaction mixture obtained from (i). Therefore, the present invention relates to the process described above, wherein the process further comprises (ii) separating the compound of formula (II) from the mixture obtained in (i).

In this context, it is conceivable that the reaction mixture obtained from (i), after separation of the catalyst, is subjected to at least one distillation stage from which the compound of formula (II) is obtained.

Depending on the nature of the solvent, optionally used in (i), it is conceivable that prior to the distillation, a phase separation is performed and the phase containing the compound of formula (II) is subjected to distillation.

The present invention is further illustrated by the following embodiments and the combination of embodiments as indicated by the respective dependencies:

1. A process for the oxidation of an organic carbonyl compound of formula (I)

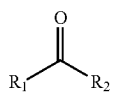

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, said process comprising (i) reacting the compound of formula (I), optionally in the presence of a solvent, with hydrogen peroxide in the presence of a catalyst comprising a tin-containing zeolitic material having an MWW-type framework structure (Sn-MWW), to obtain a compound of formula (II)

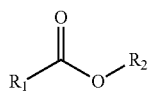

wherein, if neither $R_1$ nor $R_2$ is a hydrogen atom, $R_1$ and $R_2$ may form, together with the carbonyl group or the carboxyl group, a ring and the compound of formula (I) is

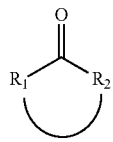

and the compound of formula (II) is

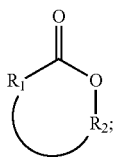

wherein the Sn-MMW framework structure comprises $SiO_2$ and $B_2O_3$ and the molar ratio of $B_2O_3$ relative to $SiO_2$ is at most 0.0025:1.

2. The process of embodiment 1, wherein $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom and wherein, if neither $R_1$ nor $R_2$ is a hydrogen atom, $R_1$ and $R_2$ may form, together with the carbonyl group or the carboxyl group, a ring having from 4 to 20 carbon atoms.

3. The process of embodiment 1 or 2, wherein the compound of formula (I) contains at least one C—C double bond.

4. The process of claim 3, wherein the compound of formula (I) contains a C—C double bond in alpha position to the carbonyl group.

5. The process of any of embodiments 1 to 4, wherein at least 95 weight-%, preferably at least 98 weight-%, more preferably at least 99 weight-% of the framework structure of the Sn-MWW consist of $B_2O_3$ and $SiO_2$, wherein the molar ratio of $B_2O_3$ relative to $SiO_2$ is in the range of from 0.0005:1 to 0.0025:1, preferably from 0.0005:1 to 0.0020:1, the Sn-MWW more preferably being free of Al.

6. The process of any of embodiments 1 to 5, wherein the Sn-MWW has a tin content in the range of from 0.1 to 4.0 weight-%, preferably from 0.1 to 3.0 weight-%, more preferably from 0.1 to 2.5 weight-%, calculated as element and based on the weight of the Sn-MWW.

7. The process of embodiment 6, wherein the Sn-MWW has a tin content in the range of from 0.1 to 1.0 weight-%, calculated as element and based on the weight of the Sn-MWW.

8. The process of embodiment 6, wherein the Sn-MWW has a tin content in the range of from 0.1 to 0.5 weight-%, calculated as element and based on the weight of the Sn-MWW.

9. The process of any of embodiments 1 to 8, wherein at the beginning of the reaction according to (i), the molar ratio of Sn, calculated as element and contained in the Sn-MWW, relative to the compound according to formula (I) is in the range of from 0.001:1 to 0.05:1, preferably from 0.003:1 to 0.3:1, more preferably from 0.005:1 to 0.01:1.

10. The process of any of embodiments 1 to 9, wherein at the beginning of the reaction according to (i), the molar ratio of Sn, calculated as element and contained in the Sn-MWW, relative to hydrogen peroxide is in the range of from 0.001:1 to 0.05:1, preferably from 0.003:1 to 0.03:1, more preferably from 0.005:1 to 0.015:1.

11. The process of any of embodiments 1 to 10, wherein in (i), the compound of formula (I) is reacted in the presence of a solvent, preferably selected from the group consisting of acetonitrile, 1,2-dichloroethane, dichloromethane, chloroform, acetonitrile, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof, the solvent more preferably being 1,2-dichloroethane.

12. The process of any of embodiments 1 to 11, wherein the reaction is carried out at a temperature in the range of from 50 to 150° C., preferably from 70 to 120° C., more preferably from 90 to 110° C.

13. The process of any of embodiments 1 to 12, wherein the reaction is carried out in batch-mode.

14. The process of embodiment 13, wherein the reaction is carried out for a period in the range of from 1 to 10 h, preferably from 3 to 5 h.

15. The process of embodiment 13 or 14, wherein the reaction is carried out in an open system under reflux.

16. The process of any of embodiments 13 to 15, wherein the catalyst is employed as powder or spray-powder, wherein preferably at least 90 weight-%, more preferably at least 95 weight-%, more preferably at least 99 weight-% of the catalyst consist of the Sn-MWW.

17. The process of any of embodiments 1 to 12, wherein the reaction is carried out in continuous-mode.

18. The process of embodiment 17, wherein the catalyst is employed as a molding comprising the Sn-MWW and preferably a binder, more preferably a silica binder, wherein the Sn-MWW is comprised in the molding preferably as powder or spray-powder.

19. The process of any of embodiments 1 to 18, wherein the process further comprises (ii) separating the compound of formula (II) from the mixture obtained in (i).
20. The process of embodiment 19, wherein the separation according to (ii) comprises a distillation stage, optionally after a phase separation stage.
21. A reaction mixture, obtainable or obtained from step (i) of the process according to any of embodiments 1 to 18.

The present invention is further illustrated by the following reference examples and examples.

EXAMPLES

Reference Example 1

General Procedure for the Preparation of the Catalyst Comprising the Sn-MWW (i) Preparation of B-MWW 470.4 kg de-ionized water were provided in a vessel. Under stirring at 70 rpm (rounds per minute), 162.5 kg boric acid were suspended in the water at room temperature. The suspension was stirred for another 3 h at room temperature. Subsequently, 272.5 kg piperidine were added, and the mixture was stirred for another hour. To the resulting solution, 492 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW had a pH of 11.3 as determined via measurement with a pH-sensitive electrode. From said suspension, the B-MWW was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:
drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower—filter—scrubber
gas flow: 1,500 kg/h
filter material: Nomex® needle-felt 20 m²
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material was then subjected to calcination at 600° C. for 10 h. The calcined material had a molar ratio $B_2O_3:SiO_2$ molar ratio of 0.04 and a crystallinity of 83%.

(ii) Deboronation 360 kg of de-ionized water and 12 kg of calcined material were refluxed at 100° C. under stirring at 70 r.p.m. for 20 h. The resulting deboronated zeolitic material was separated from the suspension by filtration and washed with 240 l deionized water at room temperature. After the filtration, the filter cake was dried at a temperature of 120° C. for 48 h.

(iii) Incorporation of Sn 675 g deionized water were provided in a glass beaker and 226.1 g piperidine were added under stirring and further stirred for 20 minutes. Separately, in a glovebox X g (see Table 1 below) of tin(IV)-tert-butoxyde were dissolved in 100 g piperidine under nitrogen atmosphere to obtain a tin-containing zeolitic material having an tin content of Y weight-% (see Table 1 below). The mixture was added to the aqueous piperidine suspension and further stirred for 10 minutes. 150 g zeolitic material obtained according to Example 1 (ii) were added to the mixture and stirred for 1 h (200 r.p.m.) at room temperature. The obtained suspension was then filled in an autoclave. The mixture was treated for 120 h at a temperature of 170° C. under stirring (100 r.p.m.). Afterwards the autoclave was cooled down to room temperature and the resulting zeolitic material was separated from the suspension by filtration at room temperature and washed with deionized water until the washing water had a conductivity of less than 300 microSiemens/cm. After the filtration, the filter cake was dried at a temperature of 120° C. for 16 h.

(iv) Acid-Treatment 150 g of the zeolitic material obtained according to Example 1 (iii) were provided in a round bottom flask and 4.5 kg of a 30 wt-% $HNO_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 16 h and calcined by heating to 550° C. (2° C. per minute) and subsequent heating at 550° C. for 10 h. The obtained tin-containing zeolitic materials having an MWW framework structure (Sn-MWW) had a $B_2O_3:SiO_2$ molar ratio of 0.0015:1.

TABLE 1

Amount of tin(IV)-tert-butoxyde (X) for the incorporation of tin in the zeolitic material and the resulting Sn content (Y) of the Sn-MWW

| X [g] | Y [weight-%] |
|---|---|
| 2.30 | 0.42 |
| 4.35 | 0.8 |
| 11.69 | 2.1 |

Example 1

Baeyer-Villiger Oxidation of Cyclohexanone to Epsilon-Caprolactone Using a Sn-MWW Having a Sn Content of 2.1 Weight-% and Acetonitrile as Solvent A glass vessel was charged with 1.5 g cyclohexanone, 45 g acetonitrile and 0.6 g zeolitic material obtained according to Reference Example 1, having a Sn content of 2.1 weight-%.

The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by GC analysis using di-n-butyl ether as internal standard.

Results of Example 1

Example 1 was carried out by a process according to the present invention, i.e. by reacting cyclohexanone in the presence of acetonitrile with hydrogen peroxide in the presence of a Sn-MWW obtained according to Reference Example 1. Thereby, epsilon-caprolactone was obtained, wherein a selectivity to epsilon-caprolactone based on cyclohexanone of 37% was achieved, determined by GC analysis using di-n-butyl ether as internal standard.

Example 2

Baeyer-Villiger Oxidation of Cyclohexanone to Epsilon-Caprolactone Using a Sn-MWW Having a Sn Content of 2.1 Weight-% and 1,2-Dichloromethane as Solvent A glass vessel was charged with 1.5 g cyclohexanone, 45 g 1,2-dichloromethane and 0.6 g zeolitic material obtained according to Reference Example 1, having a Sn content of 2.1 weight-%. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-n-butyl ether as internal standard.

Results of Example 2

Example 2 was carried out by a process according to the present invention, i.e. by reacting cyclohexanone in the presence of 1,2-dichloromethane with hydrogen peroxide in the presence of a Sn-MWW obtained according to Reference Example 1. Thereby, epsilon-caprolactone was obtained, wherein a selectivity to epsilon-caprolactone based on cyclohexanone of 55% was achieved, determined by GC analysis using di-n-butyl ether as internal standard.

Example 3

Baeyer-Villiger Oxidation of Cyclohexanone to Epsilon-Caprolactone Using a Sn-MWW Having a Sn Content of 0.42 Weight-% and Acetonitrile as Solvent A vessel was charged with 1.5 g cyclohexanone, 2.85 g zeolitic material obtained according to Reference Example 1, having a Sn content of 0.42 weight-% and 45 g acetonitrile. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-n-butyl ether as internal standard.

Results of Example 3

Example 3 was carried out by a process according to the present invention, i.e. by reacting cyclohexanone in the presence of acetonitrile with hydrogen peroxide in the presence of a Sn-MWW obtained according to Reference Example 1. Thereby, epsilon-caprolactone was obtained, wherein a selectivity to epsilon-caprolactone based on cyclohexanone of 54% was achieved, determined by quantitative GC analysis using di-n-butyl ether as internal standard.

Example 4

Baeyer-Villiger Oxidation of Cyclohexanone to Epsilon-Caprolactone Using a Sn-MWW Having a Sn Content of 0.42 Weight-% and 1,2-Dichloromethane as Solvent A vessel was charged with 1.5 g cyclohexanone, 2.85 g zeolitic material obtained according to Reference Example 1, having a Sn content of 0.42 weight-% and 45 g 1,2-dichloromethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-n-butyl ether as internal standard.

Results of Example 4

Example 4 was carried out by a process according to the present invention, i.e. by reacting cyclohexanone in the presence of 1,2-dichloromethane with hydrogen peroxide in the presence of a Sn-MWW obtained according to Reference Example 1. Thereby, epsilon-caprolactone was obtained, wherein a selectivity to epsilon-caprolactone based on cyclohexanone of 65% was achieved, determined by quantitative GC analysis using di-n-butyl ether as internal standard.

Example 5

Baeyer-Villiger Oxidation of Cyclohexanone to Epsilon-Caprolactone Using a Sn-MWW Having a Sn Content of 0.42 Weight-% and Chlorobenzene as Solvent A vessel was charged with 1.5 g cyclohexanone, 2.85 g zeolitic material obtained according to Reference Example 1, having a Sn content of 0.42 weight-% and 45 g chlorobenzene. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-n-butyl ether as internal standard.

Results of Example 5

Example 5 was carried out by a process according to the present invention, i.e. by reacting cyclohexanone in the presence of chlorobenzene with hydrogen peroxide in the presence of a Sn-MWW obtained according to Reference Example 1. Thereby, epsilon-caprolactone was obtained, wherein a selectivity to epsilon-caprolactone based on cyclohexanone of 34% was achieved, determined by quantitative GC analysis using di-n-butyl ether as internal standard.

Example 6

Baeyer-Villiger Oxidation of Cyclododecanone to Lauryllactone Using a Sn-MWW Having a Sn Content of 0.8 Weight-% and 1,2-Dichloroethane as Solvent A vessel was charged with 2.8 g cyclododecanone, 1.5 g zeolitic material obtained according to Reference Example 1, having a Sn content of 0.8 weight-% and 45 g 1,2-dichloroethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by GC analysis using di-n-butyl ether as internal standard.

Results of Example 6

Example 6 was carried out by a process according to the present invention, i.e. by reacting cyclododecanone in the presence of 1,2-dichloroethane with hydrogen peroxide in the presence of a Sn-MWW obtained according to Reference Example 1, having a Sn content of 0.8 weight-%. Thereby, lauryllactone was obtained, wherein a selectivity to lauryllactone based on cyclododecanone of 30% was achieved, determined by quantitative GC analysis using di-n-butyl ether as internal standard.

Example 7

Baeyer-Villiger Oxidation of 2-Heptylcyclopentanone to Delta-dodecalactone Using a Sn-MWW Having a Sn Content of 2.1 Weight-% and 1,2-Dichloroethane as Solvent A vessel was charged with 2.8 g 2-heptylcyclopentanone 0.6 g catalyst obtained according to Reference Example 1, having a Sn content of 2.1 weight-% and 45 g 1,2-dichloroethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by GC analysis using di-d-butyl ether as internal standard.

Results of Example 7

Example 7 was carried out by a process according to the present invention, i.e. by reacting 2-heptylcyclopentanone in the presence of 1,2-dichloroethane with hydrogen peroxide in the presence of a Sn-MWW obtained according to Reference Example 1, having a Sn content of 2.1 weight-%. Thereby, delta-dodecalactone was obtained, wherein a selectivity to delta-dodecalactone based on 2-heptylcyclopentanone of 91% was achieved, determined by quantitative GC analysis using di-n-butyl ether as internal standard.

Example 8

Baeyer-Villiger Oxidation of Citral to Melonal Using a Sn-MWW Having a Sn Content of 2.1 Weight-% and 1,2-Dichloroethane as Solvent A vessel was charged with 2.3 g citral, 0.6 g catalyst obtained according to Reference Example 1, having a Sn content of 2.1 weight-% and 45 g 1,2-dichloroethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-d-butyl ether as internal standard.

Results of Example 8

Example 8 was carried out by a process according to the present invention, i.e. by reacting citral in the presence of 1,2-dichloroethane with hydrogen peroxide in the presence of a Sn-MWW obtained according to Reference Example 1, having a Sn content of 2.1 weight-%. Thereby, melonal was obtained, wherein a selectivity to melonal based on citral of 70% was achieved, determined by quantitative GC analysis using di-n-butyl ether as internal standard.

Example 9

Baeyer-Villiger Oxidation of 4-Pentenal to 4-Pentenoic Acid Using a Sn-MWW Having a Sn Content of 2.1 Weight-% and 1,2-Dichloroethane as Solvent A vessel was charged with 1.6 g technical 4-pentenal (76 weight-%), 0.6 g catalyst obtained according to Reference Example 1, having a Sn content of 2.1 weight-% and 45 g 1,2-dichloroethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-d-butyl ether as internal standard.

Results of Example 9

Example 9 has also been carried out by a process according to the present invention, i.e. by reacting 4-pentenal in the presence of 1,2-dichloroethane with hydrogen peroxide in the presence of a Sn-MWW obtained according to Reference Example 1, having a Sn content of 2.1 weight-%. Thereby, 4-pentenoic acid was obtained, wherein a selectivity to 4-pentenoic acid based on 4-pententenal of 27% was achieved, determined by quantitative GC analysis using di-n-butyl ether as internal standard.

Reference Example 2

General Procedure for the Preparation of the Catalyst Comprising the Sn-MWW (i) as in Reference Example 1(i) Above (ii) as in Reference Example 1 (ii) Above (iii) Incorporation of Sn 776.25 g deionized water were provided in a glass beaker and 375 g piperidine were added under stirring. To this suspension 1.45 g of $Sn(OAc)_2$ (Sn(II) acetate) was added and the suspension stirred for another 10 minutes. 172.4 g zeolitic material obtained according to Example 1 (ii) were added to the mixture and stirred for 20 min (200 r.p.m.) at room temperature. The obtained suspension was than filled in an autoclave. The mixture was treated for 48 h at a temperature of 170° C. under stirring (100 r.p.m.).

Afterwards the autoclave was cooled down to room temperature and the resulting zeolitic material was separated from the suspension by filtration at room temperature and washed with deionized water until the washing water had a conductivity of less than 200 microSiemens/cm. After the filtration, the filter cake was dried at a temperature of 120° C. for 16 h.

The dried zeolitic material had a Si content of 40 weight-% and a Sn content of 0.42 weight-%.

(iv) Acid Treatment 173.4 g zeolitic material obtained according to Example 4 (iii) were provided in a round bottom flask and 5,202 g of a 30 weight-% $HNO_3$ aqueous solution, having a pH in the range from 0 to 1, were added. The mixture was stirred at a temperature of 100° C. for a period of 20 h (200 r.p.m.) under reflux. The suspension was filtered and the filter cake was then washed with de-ionized water at room temperature until the washing water had a pH of approximately 7. The obtained zeolitic material was dried at 120° C. for 16 h and calcined by heating to 550° C. (2° C. per minute) and subsequent heating at 550° C. for 10 h. The dried and calcined zeolitic material having an MWW framework structure had a Si content of 47 weight-% and a Sn content of 0.46 weight-% and a c parameter as determined via XRD of 26.91 Angstrom. Further, the zeolitic material had a BET surface area, determined according to DIN 66131 of 520 m²/g, and a Langmuir surface, determined according to DIN 66131 of 713 m²/g.

Example 10

Baeyer-Villiger Oxidation of Cyclohexanone to Epsilon-Caprolactone Using a Sn-MWW Having a Sn Content of 0.46 Weight-% and 1,2-Dichloroethane as Solvent A 100 ml glass flask vessel was charged with 1.5 g cyclohexanone, 1.2 g zeolitic material obtained according to Reference Example 2, having a Sn content of 0.46 weight-% and 45 g dichloroethane. The mixture was heated to reflux (95° C.). An aqueous solution of 0.5 g $H_2O_2$ (70 weight-%) was added and the reaction was stirred for 4 h. After cooling down to room temperature, the solution was filtrated and analyzed by quantitative GC analysis using di-n-butyl ether as internal standard.

Results of Example 10

Example 10 was carried out by a process according to the present invention, i.e. by reacting cyclohexanone in the presence of dichloroethane with hydrogen peroxide in the presence of a Sn-MWW obtained according to Reference Example 2. Thereby, epsilon-caprolactone was obtained, wherein a selectivity to epsilon-caprolactone based on cyclohexanone of 54% was achieved, determined by quantitative GC analysis using di-n-butyl ether as internal standard.

Example 11

Continuous-Type Baeyer-Villiger Oxidation of Cyclohexanone to Epsilon-Caprolactone Using a Shaped Sn-MWW Having a Sn Content of 0.46 Weight-% and Acetonitrile as Solvent (i) Preparation of B-MWW 480 kg de-ionized water were provided in a vessel. Under stirring at 70 rpm (rounds per minute), 166 kg boric acid were suspended in the water at room temperature. The suspension was stirred for another 3 h at room temperature. Subsequently, 278 kg piperidine were added, and the mixture was stirred for another hour. To the resulting solution, 400 kg Ludox® AS-40 were added, and the resulting mixture was stirred at 70 rpm for another hour at room temperature. The finally obtained mixture was transferred to a crystallization vessel and heated to 170° C. within 5 h under autogenous pressure and under stirring (50 rpm). The temperature of 170° C. was kept essentially constant for 120 h. During these 120 h, the mixture was stirred at 50 rpm. Subsequently, the mixture was cooled to a temperature of from 50-60° C. The aqueous suspension containing B-MWW had a pH of 11.3 as determined via measurement with a pH-sensitive electrode. From said suspension, the B-MWW was separated by filtration. The filter cake was then washed with de-ionized water at room temperature until the washing water had a conductivity of less than 500 microSiemens/cm. The thus obtained filter cake was subjected to spray-drying in a spray-tower with the following spray-drying conditions:
drying gas, nozzle gas: technical nitrogen
temperature drying gas:
 temperature spray tower (in): 235° C.
 temperature spray tower (out): 140° C.
nozzle:
 top-component nozzle supplier Gerig; size 0
 nozzle gas temperature: room temperature
 nozzle gas pressure: 1 bar
operation mode: nitrogen straight
apparatus used: spray tower with one nozzle
configuration: spray tower—filter—scrubber
gas flow: 1,500 kg/h
filter material: Nomex® needle-felt 20 m²
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 650° C. in a rotary oven in contra current flow (0.8-1 kg/h). The calcined material had a B content of 1.4 weight-%, a Si content of 43 wt. %, and TOC of less than 0.1 wt. %. The material had a BET specific surface area, measured according to DIN 66131, of 468 m²/g.

(ii) Deboronation 1,590 kg of de-ionized water and 106 kg of the calcined material obtained from (i) were refluxed at 100° C. under stirring at 70 r.p.m. for 10 h. The resulting deboronated zeolitic material was separated from the suspension by filtration and washed 4 times with 150 l deionized water at room temperature. After the filtration, the filter cake was dried at a temperature of 120° C. for 16 h. The dried zeolitic material having an MWW framework structure had a B content of 0.04 weight-%, a Si content of 42 weight-%, and a BET specific surface area, measured according to DIN 66131, of 462 m²/g.

(iii) Incorporation of Sn 776.25 g deionized water were provided in a glass beaker and 375 g piperidine were added under stirring. To this suspension 2.5 g of Sn(IV)butoxyde predissolved in 25 g piperidine were added and the suspension was stirred for another 10 minutes. 172.4 g deboromated zeolitic material obtained according to (ii) above were added to the mixture and stirred for 60 min (200 r.p.m.) at room temperature. The obtained suspension was than filled in an autoclave. The mixture was treated for 120 h at a temperature of 170° C. under stirring (100 r.p.m.). Afterwards the autoclave was cooled down to room temperature and the resulting zeolitic material was separated from the suspension by filtration at room temperature and washed with deionized water until the washing water had a conductivity of less than 200 microSiemens/cm. After the filtration, the filter cake was dried at a temperature of 120° C. for 16 h. The dried zeolitic material had a Si content of 40 weight-% and a Sn content of 0.42 weight-%.

(iv) Acid Treatment 174 g tin containing zeolitic material obtained from (iii) above were provided in a round bottom flask and 5,220 kg of a 30 weight-% $HNO_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 16 h and calcined by heating to 550° C. (2 K/min) and subsequent heating at 550° C. for 10 h.

The dried and calcined zeolitic material hat a Si content of 49 weight-% and a Sn content of 0.46 weight-% and a c parameter as determined via XRD of 27.1 Angstrom. Further, the zeolitic material had a BET surface area, determined according to DIN 66131, of 521 m²/g, a Langmuir surface, determined according to DIN 66131 of 695 m²/g.

(v) Preparation of a Molding 140 g of the zeolitic calcined zeolitic material obtained from (iv) and 8.4 g Walocel were kneaded for 5 min in an edge mill. During kneading, 82.6 g Ludox® AS-40 were added continuously. After 10 min, the addition of 150 ml de-ionized water was started. After another 30 min, die kneading mass was adjusted by addition of 30 ml de-ionized water. After a total kneading time of 50 min, the mass is extrudable, and the mass was extruded at a pressure of from 100 to 150 bar during 1 min. The obtained strands were dried at 120° C. for 8 h in an oven and calcined at 500° C. for 5 h. 137.2 g of white strands were obtained, having a diameter of 1.7 mm. The dried and calcined material in the form of said strands had a Si content of 46 weight-%, a Sn content of 0.41 weight-% and TOC of 0.01 weight-%. Further, the strands had a BET surface area, determined according to DIN 66131, of 412 m²/g, and a pore volume determined by Hg porosimetry of 0.91 ml/g.

(vi) Test of the Shaped Material of in the Baeyer-Villiger Oxidation of Cyclohexanone to Epsilon-Caprolactone in Acetonitrile as Solvent A tubular reactor (length: 1.4 m, internal diameter: 7 mm) equipped with a jacket for thermostatization was charged with 15 g of the catalyst obtained from (v) above in the form of strands with a diameter of 1.7 mm. The remaining reactor volume was filled with inert material (steatite spheres, 2 mm in diameter, to a height of about 5 cm at the lower end of the reactor and the remainder at the top end of the reactor). The reactor was thermostatized by flowing a heat transfer medium, a mixture of water and ethylene glycol, through the jacket. The heat transfer medium was fed at the lower end of the jacket so that it flew in cocurrent mode to the reactor contents. The temperature of the heat transfer medium at the entrance of the jacket is defined as the reaction temperature. The flow rate of the heat transfer medium was adjusted so that the difference between entrance and exit temperature was at most 1 K. Pressure in the reactor was controlled by a suitable pressure control valve and maintained constant at 20 bar (abs).

The reactor feed stream was metered by using a metering pump. The stream consisted of a mixture of acetonitrile (93.6 weight-%), cyclohexanone (2.5 weight-%), an aqueous hydrogen peroxide solution with a concentration of 40 weight-% (3.9 weight-%) (flow rate: 40 g/h). Under the conditions used the feed was liquid and only one liquid phase was present.

The experiment was performed in a continuous manner. At the start of the run (t=0 is defined at which the metering pump was started) the reaction temperature was set to 90° C. After a certain period of time (usually within 4 hours on stream) a stationary state was reached. The reactor effluent after the pressure control valve was collected, weighed and analyzed by GC using di-n-butylether as internal standard.

Epsilon-caprolactone was obtained, wherein a selectivity to epsilon-caprolactone based on cyclohexanone of 40% was achieved.

Summary of the Examples

Comparison of the examples 1 to 5 and 10, i.e. comparison of the examples using cyclohexanone as starting material and acetonitrile or 1,2-dichloroethane, respectively, as solvent clearly show that the highest selectivity to the Baeyer-Villiger reaction product, i.e. epsilon-caprolactone, is achieved when using 1,2-dichloroethane as solvent. The use of 1,2-dichloroethane as solvent according to examples 2 and 4, leads to a higher selectivity to epsilon-caprolactone compared with the use of acetonitrile as solvent according to examples 1 and 3. Further, in example 5, chlorobenzene is used as solvent in the Baeyer-Villiger reaction. However, in this case the selectivity to epsilon-caprolactone is significantly lower than if acetonitrile is used as solvent (examples 1 and 3) even lower than if 1,2-dichloroethane is used as solvent (examples 2 and 4).

Further, comparison of examples 1 and 2, using a Sn-MWW having a Sn content of 2.1 weight-% with examples 3 and 4, using a Sn-MWW with a Sn content of 0.42 weight-% show that the selectivity to the Baeyer-Villiger reaction product, i.e. epsilon-caprolactone, increases by use of the Sn-MWW with a Sn content of 0.42 weight-%. Thus, it was shown that the novel Sn-MWW material of the present invention having an increased interlayer distance is particularly preferred as catalyst.

Further, examples 6 and 7 show that according to the process of the present invention, also cyclic ketones can be oxidized in a Baeyer-Villiger reaction. Furthermore, examples 8 and 9 show that according to the process of the present invention, also unsaturated compounds can be oxidized in a Baeyer-Villiger reaction. In particular, example 8 shows that alpha, beta-unsaturated aldehydes can be oxidized in a Baeyer-Villiger reaction to obtain an aldehyde, wherein a very high selectivity of 70% is achieved.

In example 11, it is shown that the inventive concept is also a very good option for continuous-type processes which are of particular relevance for industrial purposes.

Cited Literature

Justus Liebigs Ann. Chem. 681 (1965) pages 28-30
Nature 412 (2001) pages 423-425
Journal of Catalysis 234 (2005) pages 96-100
Microporous and Mesoporous Materials 165 (2013) pages 210-218
U.S. Pat. No. 5,968,473
U.S. Pat. No. 6,306,364
WO03/074422 A1
U.S. Pat. No. 7,326,401 B2

The invention claimed is:

1. A process for the oxidation of an organic carbonyl compound of formula (I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, wherein, if neither $R_1$ nor $R_2$ is a hydrogen atom, $R_1$ and $R_2$ may form, together with the carbonyl group, a ring such that the compound of formula (I) is

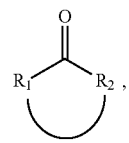

said process comprising (i) reacting the compound of formula (I), optionally in the presence of a solvent, with hydrogen peroxide in the presence of a catalyst comprising a tin-containing zeolitic material having an MWW-type framework structure (Sn-MWW), wherein the Sn-MMW framework structure comprises $SiO_2$ and $B_2O_3$ and the molar ratio of $B_2O_3$ relative to $SiO_2$ is at most 0.0025:1,
to obtain a compound of formula (II)

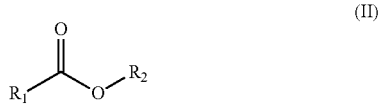

wherein, if neither $R_1$ nor $R_2$ is a hydrogen atom, $R_1$ and $R_2$ may form, together with the carbonyl group or the carboxyl group, a ring such that the compound of formula (II) is

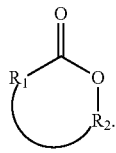

2. The process of claim 1, wherein $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom and wherein, if neither $R_1$ nor $R_2$ is a hydrogen atom, $R_1$ and $R_2$ may form, together with the carbonyl group or the carboxyl group, a ring having from 4 to 20 carbon atoms.

3. The process of claim 1, wherein the compound of formula (I) contains at least one C—C double bond.

4. The process of claim 3, wherein the compound of formula (I) contains a C—C double bond in alpha position to the carbonyl group.

5. The process of claim 1, wherein at least 99 weight-% of the framework structure of the Sn-MWW consist of $B_2O_3$ and $SiO_2$, wherein the molar ratio of $B_2O_3$ relative to $SiO_2$ is in the range of from 0.0005:1 to 0.0025:1.

6. The process of claim 1, wherein the Sn-MWW has a tin content in the range of from 0.1 to 4.0 weight-%, calculated as element and based on the weight of the Sn-MWW.

7. The process of claim 1, wherein the Sn-MWW has a tin content in the range of from 0.1 to 1.0 weight-% or in the range of from 0.1 to 0.5 weight-%, calculated as element and based on the weight of the Sn-MWW.

8. The process of claim 1, wherein at the beginning of the reaction according to (i), the molar ratio of Sn, calculated as element and contained in the Sn-MWW, relative to the compound according to formula (I) is in the range of from 0.001:1 to 0.05:1.

9. The process of claim 1, wherein at the beginning of the reaction according to (i), the molar ratio of Sn, calculated as element and contained in the Sn-MWW, relative to hydrogen peroxide is in the range of from 0.001:1 to 0.05:1.

10. The process of claim 1, wherein in (i), the compound of formula (I) is reacted in the presence of a solvent, selected from the group consisting of acetonitrile, 1,2-dichloroethane, dichloromethane, chloroform, acetonitrile, propionitrile, 1,4-dioxane, methyl tert-butyl ether, diethyl ether, dibutyl ether, ethyl acetate, butyl acetate, dimethyl carbonate, ethylene carbonate, propylene carbonate, and mixtures of two or more thereof.

11. The process of claim 1, wherein the reaction is carried out at a temperature in the range of from 50 to 150° C.

12. The process of claim 1, wherein the reaction is carried out in batch-mode.

13. The process of claim 12, wherein the reaction is carried out for a period in the range of from 1 to 10 h.

14. The process of claim 12, wherein the reaction is carried out in an open system under reflux.

15. The process of claim 12, wherein the catalyst is employed as powder or spray-powder, wherein at least 90 weight-% of the catalyst consist of the Sn-MWW.

16. The process of claim 1, wherein the reaction is carried out in continuous-mode.

17. The process of claim 16, wherein the catalyst is employed as a molding comprising the Sn-MWW and a binder, wherein the Sn-MWW is comprised in the molding as powder or spray-powder.

18. The process of claim 1, wherein the process further comprises
(ii) separating the compound of formula (II) from the mixture obtained in (i).

19. The process of claim 18, wherein the separation according to (ii) comprises a distillation stage, optionally after a phase separation stage.

20. A reaction mixture, obtained from step (i) of the process according to claim 1.

* * * * *